(12) United States Patent
Teichman et al.

(10) Patent No.: US 7,709,048 B2
(45) Date of Patent: May 4, 2010

(54) METHOD AND APPARATUS FOR COATING A MEDICAL DEVICE

(75) Inventors: Eyal Teichman, Hod-Hasharon (IL); Avner Schrift, Rishon-Le-Zion (IL)

(73) Assignee: Labcoat, Ltd. (IE)

( * ) Notice: Subject to any disclaimer, the term of this patent is extended or adjusted under 35 U.S.C. 154(b) by 1180 days.

(21) Appl. No.: 10/982,408

(22) Filed: Nov. 5, 2004

(65) Prior Publication Data

US 2006/0073265 A1    Apr. 6, 2006

Related U.S. Application Data

(63) Continuation-in-part of application No. 10/210,714, filed on Jul. 30, 2002, now Pat. No. 7,048,962, which is a continuation-in-part of application No. 10/136,295, filed on May 2, 2002, now Pat. No. 6,645,547.

(51) Int. Cl.
B05C 11/00 (2006.01)
B05D 3/12 (2006.01)

(52) U.S. Cl. ................... 427/2.24; 427/2.1; 118/669; 118/676; 118/679; 118/680

(58) Field of Classification Search ............. 427/2.1, 427/2.24; 118/668–669, 676, 679–680
See application file for complete search history.

(56) References Cited

U.S. PATENT DOCUMENTS 4,842,887 A    6/1989   Bolte 5,429,682 A *  7/1995   Harlow et al. ............ 118/681

(Continued)

FOREIGN PATENT DOCUMENTS

WO    WO 02/14078 A2    2/2002

(Continued)

OTHER PUBLICATIONS

"A Bit of Theory; What happens when a droplet hits a liquid surface? Why microdispensing needs highly dynamic systems. What makes the microdrop systems act as a pump?," www.microdrop.de/html/a_bit_of_theory.html, Nov 7, 2002, pp. 1-3.

(Continued)

*Primary Examiner*—Timothy H Meeks
*Assistant Examiner*—Cachet I Sellman
(74) *Attorney, Agent, or Firm*—Vidas, Arrett & Steinkraus, P.A.

(57) ABSTRACT

A method and device, for use in an operating theater just prior to implantation, for selectively applying a medical coating to an implantable medical device. Disclosed is a device for use with a stent deployed on a catheter balloon configured to apply a medical coating of a desired thickness to the surface of the stent only. A drop-on-demand inkjet printing system in association with an optical scanning device is described. The device is further configured to apply a plurality of layered coats, each layered coat being of a different coating material, and if appropriate, different thickness and to coat a portion of the medical device as a function of its geometric configuration. The coating is applied by moving an applicator over the device in a path that is independent of the deposited coating pattern.

19 Claims, 29 Drawing Sheets

U.S. PATENT DOCUMENTS

| | | | |
|---|---|---|---|
| 5,596,503 A * | 1/1997 | Flint | 700/118 |
| 5,634,129 A | 5/1997 | Dickinson | |
| 5,640,587 A | 6/1997 | Davis et al. | |
| 5,649,139 A | 7/1997 | Weinreb et al. | |
| 5,652,884 A | 7/1997 | Palevich | |
| 5,706,517 A | 1/1998 | Dickinson | |
| 5,710,896 A | 1/1998 | Seidl | |
| 5,713,045 A | 1/1998 | Berdahl | |
| 5,717,877 A | 2/1998 | Orton et al. | |
| 5,729,671 A | 3/1998 | Peterson et al. | |
| 5,732,229 A | 3/1998 | Dickinson | |
| 5,734,852 A | 3/1998 | Zias et al. | |
| 5,737,559 A | 4/1998 | Orton et al. | |
| 5,752,245 A | 5/1998 | Parrish et al. | |
| 5,755,781 A | 5/1998 | Jayaraman | |
| 5,758,153 A | 5/1998 | Atsatt et al. | |
| 5,848,291 A | 12/1998 | Milne et al. | |
| 5,857,064 A | 1/1999 | deSilva | |
| 5,871,436 A | 2/1999 | Eury | |
| 5,877,768 A | 3/1999 | Jain | |
| 5,891,507 A | 4/1999 | Jayaraman | |
| 5,922,393 A | 7/1999 | Jayaraman | |
| 5,936,643 A | 8/1999 | Tindell et al. | |
| 5,972,027 A | 10/1999 | Johnson | |
| 6,001,311 A | 12/1999 | Brennan | |
| 6,042,600 A | 3/2000 | Rosenthal et al. | |
| 6,106,454 A | 8/2000 | Berg et al. | |
| 6,129,658 A | 10/2000 | Delfino et al. | |
| 6,169,550 B1 | 1/2001 | Jain | |
| 6,171,232 B1 | 1/2001 | Papandreou et al. | |
| 6,203,551 B1 | 3/2001 | Wu | |
| 6,214,115 B1 | 4/2001 | Taylor et al. | |
| 6,235,340 B1 | 5/2001 | Lee et al. | |
| 6,245,104 B1 | 6/2001 | Alt | |
| RE37,258 E | 7/2001 | Patel et al. | |
| 6,254,632 B1 | 7/2001 | Wu et al. | |
| 6,280,411 B1 | 8/2001 | Lennox | |
| 6,287,628 B1 | 9/2001 | Hossainy et al. | |
| 6,290,722 B1 | 9/2001 | Wang | |
| RE37,418 E | 10/2001 | Tindell et al. | |
| 6,306,166 B1 | 10/2001 | Barry et al. | |
| 6,309,380 B1 | 10/2001 | Larson et al. | |
| 6,312,406 B1 | 11/2001 | Jayaraman | |
| 6,315,792 B1 | 11/2001 | Armstrong et al. | |
| 6,335,029 B1 | 1/2002 | Kamath et al. | |
| 6,341,293 B1 | 1/2002 | Hennessey | |
| 6,341,907 B1 | 1/2002 | Katsuyoshi | |
| 6,368,658 B1 | 4/2002 | Schwarz et al. | |
| 6,395,326 B1 * | 5/2002 | Castro et al. | 427/2.24 |
| 6,676,987 B2 * | 1/2004 | Zhong et al. | 427/2.24 |
| 6,689,219 B2 | 2/2004 | Birmingham | |
| 2003/0054090 A1 | 3/2003 | Hansen | |
| 2003/0144727 A1 | 7/2003 | Rosenthal et al. | |
| 2004/0249445 A1 | 12/2004 | Rosenthal et al. | |
| 2005/0113903 A1 | 5/2005 | Rosenthal et al. | |

FOREIGN PATENT DOCUMENTS

WO    WO2004/037443 A1    5/2004

OTHER PUBLICATIONS

Cooley, Patrick et al., "Applications of Ink-Jet Printing Technology to BioMEMS and Microfluidic Systems," Proceedings, SPIE Conference on Microfluidics and BioMEMS, Oct 2001, pp. 1-12.

"MicroDrop MicrodosIng System," MicroDrop Products, www.microdrop.de/html/microdropoprod.html, Nov 8, 2002, pp. 1-2.

"MicroDrop Dispenser Heads," MicroDrop Products, www.microdrop.de/html/dispenser_heads.html, Nov 8, 2002, pp. 1-2.

* cited by examiner

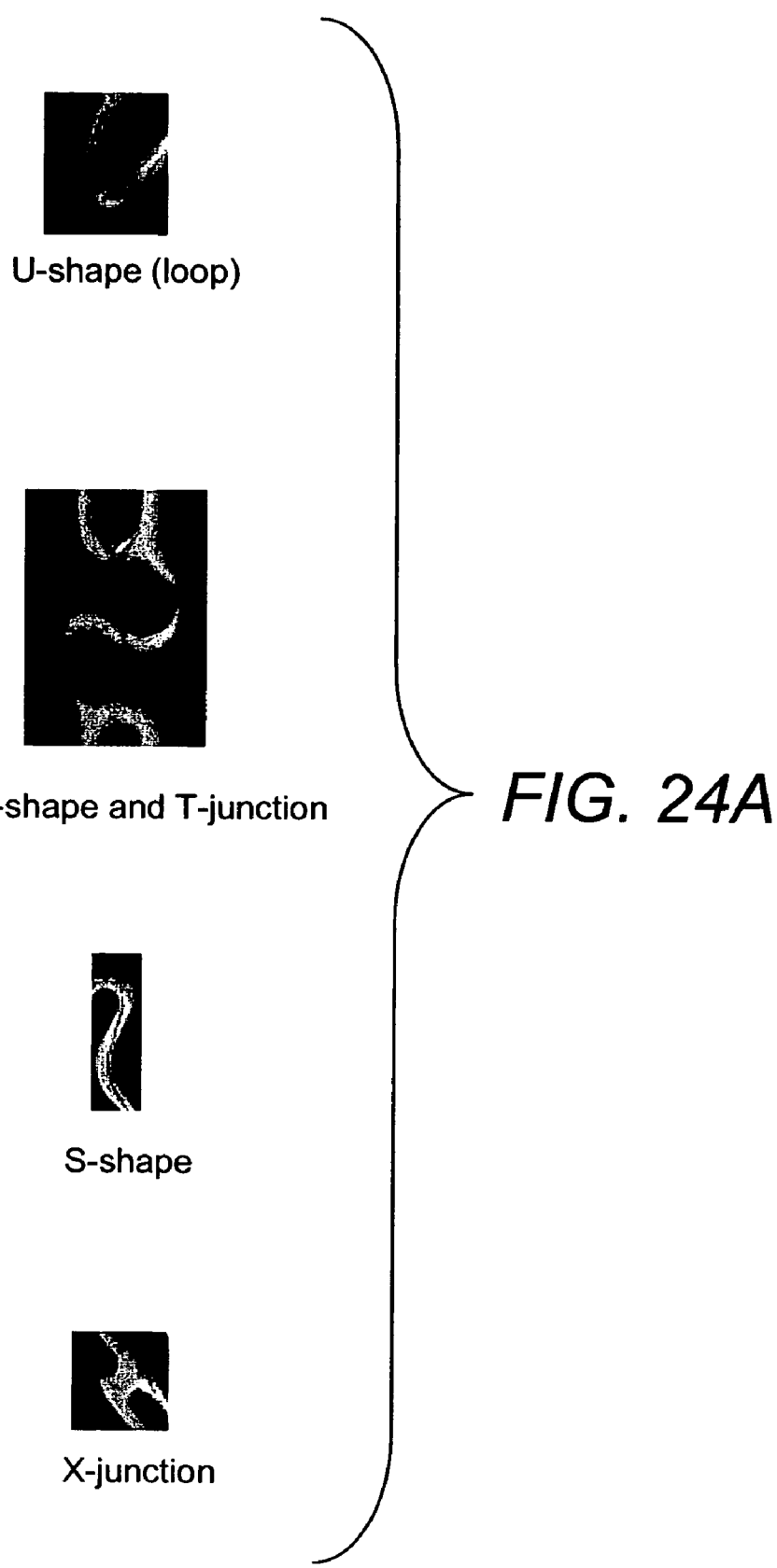

METHOD AND APPARATUS FOR COATING A MEDICAL DEVICE

RELATED APPLICATIONS

This is a continuation-in-part of U.S. patent application Ser. No. 10/210,714, filed on Jul. 30, 2002 which is a continuation-in-part of U.S. patent application Ser. No. 10/136,295, filed on May 2, 2002 each of which is incorporated herein by reference.

FIELD OF THE INVENTION

The present invention relates to coating medical devices intended for in vivo deployment and, in particular, a method and device suitable for use, just prior to implantation, for selectively applying a medical coating to an implantable medical device, for example, a stent.

DEFINITIONS

The term "prosthesis" refers to any one of many medical coating applications, including but not limited to, coronary stents, peripheral vascular stents; abdominal aortic aneurysm (AAA) devices, biliary stents and catheters, TIPS catheters and stents, vena cava filters, vascular filters and distal support devices and emboli filter/entrapment aids, vascular grafts and stent grafts, gastro enteral tubes/stents, gastra enteral and vascular anastomotic devices, urinary catheters and stents, surgical and wound drainings, radioactive needles and other indwelling metal implants, bronchial tubes and stents, vascular coils, vascular protection devices, tissue and mechanical prosthetic heart valves and rings, arterial-venous shunts, AV access grafts, surgical tampons, dental implants, CSF shunts, pacemaker electrodes and leads, suture material, wound healing, tissue closure devices including wires, staplers, surgical clips etc., IUDs and associated pregnancy control devices, ocular implants, timponoplasty implants, hearing aids including cochlear implants, implantable pumps, e.g., insulin pumps, implantable cameras and other diagnostic devices, drug delivery capsules, left ventricular assist devices (LVADs) and other implantable heart support and vascular systems, indwelling vascular access catheters and associated devices, e.g., ports, maxilo fascial implants, orthopedic implants, e.g., joint replacement, trauma management and spine surgery devices, implantable devices for plastic and cosmetic surgery, implantable meshes, e.g., for hernia or for uro-vaginal repair, brain disorders, and gastrointestinal ailments.

The term "drop-on-demand", as used herein, refers to any active or passive release of a predetermined drop or number of drops equivalent to a desired quantity of coating material, e.g., a coating material to be placed on a prosthesis. Drop-on-demand also refers to jetting when a sequence of drops is released. One example of "drop-on-demand" is the piezoelectric drop-on-demand technology manufactured by Ink Jet Technology, Inc. of San Jose, Calif. which provides applicators for a wide variety of coating applications. The micromachined ceramic design of this technology is robust and chemically inert to almost every kind of fluid and coating and is compatible with a wide range of fluids having extreme pH values or strong solvent characteristics. Non-Newtonian fluids are also compatible with such devices due to the internal design of the applicator allowing laminar flow of the fluid. With a built in heater and high temperature operating potential, piezo drop-on-demand applicators are compatible with a wide variety of coating materials. In addition, acoustic droplet dispensing devices as, for example, those described by Xerox Corporation at http://www.parc.xerox.com/research/dhl/projects/dropletdispensing/acoustic.html may also be used.

The term "detector" or "detecting" refers to any device or method which uses energy, such as magnetic, electrical, heat, light, etc., to determine whether a target at a desired location on the prosthesis has been located and signals the applicator to drop-on-demand or identifies a location as one to be coated. The detector may or may not determine a location of the applicator relative to the target to provide feedback for positioning the applicator. The detector determines the points on the coordinate table for desired locations on the prosthesis by providing signals for the applicator controller that are immediately used or stored as coordinate tables. Examples of detectors are light sensitive devices such as CCD area cameras, CCD line cameras, high-resolution CMOS area cameras, or devices that can capture light reflected or transmitted by the prosthesis, and electrically sensitive devices such as capacitance detectors.

The term "applicator" or "applying" refers to any configuration, apparatus, or method for positioning a coating material to a surface from a reservoir such as a point source including but not limited to a nozzle, a dispenser, or tip, or a multipoint source. An example of an applicator is a drop-on-demand ink-jet.

The term "on-the-fly" refers to translation and drop-on-demand delivery that is synchronous or close to synchronous, and/or simultaneous or close to simultaneous. Unlike freestyle movement which requires stopping for validation of preceding and subsequent movement with relation to the prosthesis, on-the-fly continues to next movement without validation step. FIG. 13 illustrates an example of on-the-fly drop-on-demand with an embodiment where the axis of rotation 700 is stationery and applicator is moving in the Z axis. A servo controller 705 directs the Z drive 710 which is coupled to applicator 725 while monitoring the velocity and location of the applicator 725 via feedback device 715. The servo controller 705 keeps the Z drive 710 within predetermined limits of the required velocity and signals the applicator controller 720 to activate the drop-on-demand applicator using data from feedback device 715 with reference to coordinates from the pre-scan by a detector determining points to be coated. In this procedure the validation of the Z position of the applicator 725 is done in real-time by the servo controller 705. The servo controller 705 interacts with the axis of rotation to determine the next location based on the last location and the time which it takes Z drive 710 to move applicator 725 to the next location. Feedback device 715 provides feedback that is an internal servo-based logic procedure and is not connected to the actual location relative to the prosthesis and therefore does not become a validation step as discussed above. In alternative embodiments, the servo controller 705, Z drive 710, Z location feedback device 715, the applicator controller 720, and the applicator 725 can be all bundled into the application control module (not shown).

The term "freestyle" refers to movement of an applicator over a portion of a prosthesis to be coated that requires validation through a predetermined user selected pattern and/or a feedback loop of applicator position relative to the portion of the prosthesis to be coated. Validation is done prior to delivery of the coating material. In one embodiment, freestyle movement moves the applicator over a predetermined position based on a user selected pattern. The position of the applicator is verified relative to the prosthesis and a new location is calculated. The applicator is moved to a new and more accurate location. The applicator delivers the coating material and then moves to the next predetermined location based on the user selected pattern.

It is noted that, as used in this specification and the appended claims, the singular forms "a," "an," and "the" include plural referents unless expressly and unequivocally limited to one referent. Thus for example, reference to "an applicator" includes two or more applicators, but "n is an integer from 1 to 60" means that n is one integer because that is limited to one integer. Also noted that as used herein, the term "polymer" is meant to refer to oligomers, homopolymers, and copolymers. The term "therapeutic agent" is meant to refer to drugs, therapeutic materials, diagnostic materials, inert ingredients, active ingredients, and inactive ingredients.

For the purposes of this specification and appended claims, unless otherwise indicated, all numbers expressing quantities of ingredients or percentages or proportions of other materials, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

BACKGROUND OF THE INVENTION

The practice of coating implantable medical devices with a synthetic or biological active or inactive agent is known. Numerous processes have been proposed for the application of such a coating. Soaking or dipping the implantable device in a bath of liquid medication is suggested by U.S. Pat. No. 5,922,393 to Jayaraman while soaking in an agitated bath is suggested by U.S. Pat. No. 6,129,658 to Delfino et al. Devices introducing heat and/or ultrasonic energy in conjunction with the medicated bath are disclosed in U.S. Pat. No. 5,891,507 to Jayaraman and U.S. Pat. No. 6,245,4 BI to Alt. U.S. Pat. No. 6,214,1 BI to Taylor et al. suggests spraying the medication by way of pressurized nozzles.

Initially such coatings were applied at the time of manufacture of the medical device. For various reasons, such as the short shelf life of some drugs combined with the time span from manufacture to implantation and the possible decision of the medical staff involved concerning the specific drug and dosage to be used based on the patient's condition at the time of implantation, a need has arisen for technologies which permit applying a coating just prior to implantation. Wrapping the implantable device with medicated conformal film is disclosed in U.S. Pat. No. 6,309,380 BI to Larson et al. Dipping or soaking in a medicated bath just prior to implantation is suggested in U.S. Pat. No. 5,871,436 to Eury, U.S. Pat. No. 6,6,454 to Berg et al., and U.S. Pat. No. 6,1171,232 BI to Papandreou et al. U.S. Pat. No. 6,3,551 BI to Wu provides a bathing chamber for use with specific implantable device such as a stent deployed on the balloon of a catheter.

Each of the methods and devices intended for use just prior to implantation, listed above, deposits the coating material onto any and all surfaces that are exposed to the coating. This may result in depositing coating material on surfaces on which the coating is unwanted or undesirable. Further, the coating may crack or break away when the implantable device is removed from the implantation apparatus. An example of this would be a stent deployed on a catheter balloon. As the balloon is inflated and the stent is expanded into position, the coating may crack along the interface between the stent and the balloon. These cracks may lead to a breaking away of a portion of the coating from the stent itself. Similar problems can occur in cases where the coating technique fails to prevent inadvertent overlapping with the edges, internal surfaces along the edges, of various devices, e.g., struts of stents. This, in turn, may affect the medicinal effectiveness of the coating, and negatively affect the entire medical procedure.

It is known to use ink-jet technology to apply a liquid to selected portion of a surface. In the paper "Applications of Ink-Jet Printing Technology to BioMEMS and Microfluidic Systems," presented at the SPIC Conference on Microfluidics and BioMEMS, October, 01, the authors, Patrick Cooley, David Wallace, and Bogdan Antohe provide a fairly detailed description of ink-jet technology and the range of its medically (the "Cooley paper") related applications, http://www.microfab.compapers/papers_pdf/spie
biomems_O1_reprint.pdf.

A related device is disclosed in U.S. Pat. No. 6,001,311 to Brennan, which uses a moveable two-dimensional array of nozzles to deposit a plurality of different liquid reagents into receiving chambers. In the Cooley paper and the device of Brennan, the selective application of the material is based on an objective predetermined location for deposit rather that on a "subjective placement" as needed to meet the requirements of a specific application procedure. With regard to the application of coatings applied to medical devices with inkjet applicators, it is possible to coat only a chosen portion of a device, such as only the stent mounted on a catheter, but not the catheter itself. This type of procedure using current technologies may, however, require providing complex data files, such as a CAD image of the device to be coated, and insuring that the device be installed in the coating apparatus in a precise manner so as to be oriented exactly the same as the CAD image.

Other systems which use ink-jet applicators apply the coating with a "freestyle" procedure. The freestyle points are determined by a preprogrammed user selected pattern that is unique to the particular shape or contour for the type of prosthesis and the desired coating to be achieved, much like a vector based printing approach. The ink-jet nozzle or prosthesis move in three-dimensions with the aid of a motion control system. The motion control system enables the ink-jet nozzle to move over the portions of the prosthesis to be sprayed. Alternatively, a real-time picture can be taken with a camera to determine the position of the ink-jet nozzle in relation to the prosthesis. Based upon the feedback of nozzle location, the ink-jet applicator can be controlled by activating the spray, moving the ink-jet nozzle, and/or moving the prosthesis to adjust to the pattern to better conform with the actual prosthesis.

This type of system is particularly inefficient because the preprogrammed user selected pattern fails to accommodate inherent variability in the surface of the prosthesis. In one non-limiting embodiment, for example, a stent crimped around a balloon catheter will not be crimped such that it has the same surface each time. The crimping cannot be determined from the factory according to the manufacturer's specifications of the stent. Further, using this type of feedback loop serves merely as a "first impression" to control the spraying, nozzle position, and/or prosthesis position, and freestyle systems consequently increase the time required to apply the coating. In the operating theatre, this delay is undesired because many types of coatings, e.g., paclitaxel, rapamycin, or several other pharmaceutical compounds or bioactive agents have to be applied to the stent crimped on the balloon catheter immediately prior to surgery.

The significance of delivering drug-loaded prostheses may offer savings benefit in time and cost. Studies have been conducted to show the importance of delivering the correct drug dose density on coronary stents to prevent restenosis by application of paclitaxel or rapamycin. Kandazari, David E. et al., *Highlights from American Heart Association Annual Scientific Sessions* 2001: *Nov.* 11 *to* 14, 2001, American Heart Journal 143 (2), 217-228, 2002; Hiatt, Bonnie L. et al., *Drug-Eluting Stents for Prevention of Restenosis: In Quest for the Holy Grail*, Catheterization and Cardiovascular Interventions 55:409-417, 2002; Kalinowski, M. et al., *Paclitaxel Inhibits Proliferation Of Cell Lines Responsible For Metal Stent Obstruction: Possible Topical Application In Malignant Bile Duct Obstructions*, Investigational Radiology 37(7):399-404, 2002. Other studies have shown how accuracy of dose related to cytotoxicity of coating drugs. Liebmann, J. E. et al., *Cytotoxic Studies Of Paclitaxel (Taxol) In Human Tumor Cell Lines*, Br. J. Cancer, 68(6):1104-9, 1993; Adler, L. M. et al., *Analysis Of Exposure Times And Dose Escalation Of Paclitaxel In Ovarian Cancer Cell Lines*, Cancer, 74(7):1891-8, 1994; Regar, E. et al., *Stent Development And Local Drug Delivery*, Br. Med. Bulletin, 59:227-48, 2001. See also http://www.tctmd.com/expert-presentations: Farb, A., *Comparative Pathology Of Drug Eluting Stents: Insights Into Effectiveness And Toxicity From Animal Lab*, CRF Drug-Eluting Stent Symposium 2002; Grube, E., *Taxol-Eluting Stent Trials*, ISET 2002 Miami Beach, Mar. 19-23, 2002 (The effect of taxol on the edges of the stent and dose response screening); Carter, Andrew J., *Sirolimus: Pre-Clinical Studies—Evaluation Of Dosing, Efficacy And Toxicity*, TCT September 2001.

SUMMARY OF THE INVENTION

The present invention is a method and device, which is suitable for use in an operating theater just prior to implantation, for selectively applying a medical coating to an implantable medical device, for example, a stent.

The present invention provides for optically scanning an object to produce a digitized representation of the object; processing the digitized representation to distinguish a first portion of the object from a second portion of the object; determining a first set of locations in a first coordinate system for a plurality of locations on the first portion of the object; and converting the first set of locations in the first coordinate system to a corresponding second set of locations in a second coordinate system.

In one embodiment, each set in the first set of locations in the first coordinate system comprises a pixel location in the digitized representation; and each set in the second set of locations in the second coordinate system comprises a linear component and a radial component.

In another embodiment of the present invention, a method of coating a medical device, includes generating an image of the medical device; processing the generated image to determine a topology of the medical device; defining a first plurality of locations on the determined topology at which at least one drop of a coating material is to be placed; converting the first plurality of locations to a corresponding second plurality of locations, each location of the second plurality of locations representing a physical location on the medical device; and depositing at least one drop of coating material at each location in the second plurality of locations.

According to yet another embodiment of the present invention, coating is applied as a function of a local, as to the stent, geometrical characteristic. Accordingly, a method optically scans an object to produce a digitized (electronic) representation of the object; processes the digitized representation to distinguish a first portion of the object from a second portion of the object; identifies at least one feature area of the first portion of the object and determines a type of the identified at least one feature area; and determines at least one characteristic of a coating material to be placed at the identified at least one feature area of the first portion of the object as a function of the determined type.

BRIEF DESCRIPTION OF THE DRAWINGS

The invention is herein described, by way of example only, with reference to the accompanying drawings, wherein:

FIGS. 24A and 24B are representations of geometrical regions of a stent;

DETAILED DESCRIPTION

The present invention is a method and device, which is suitable for use in an operating theater just prior to implantation, for selectively applying a medical coating to an implantable medical device, for example, a stent.

The principles and operation of a coating device according to the present invention may be better understood with reference to the drawings and the accompanying description.

By way of introduction, the embodiment discussed herein is a device for applying a medical coating to a stent deployed on a catheter, the coating being applied just prior to implantation and, if desired, in the operating theater. The use of optical scanning devices enables a processing unit to distinguish between the surface area of the stent and the surface area of the catheter. The processing unit selectively activates the coating applicator so as to apply the coating to substantially only the stent and not the balloon or other portion of the catheter. The coating applicator discussed herein is, by non-limiting example, a pressure-pulse actuated drop-ejection system with at least one nozzle. A readily available pressure-pulse actuated drop-ejection system, which is well suited for the present invention, is a drop-on-demand inkjet system. It should be noted, however, that any coating application system that may be selectively activated is within the intentions of the present invention. While the discussion herein is specific to this embodiment, which is intended for use in an operating theater, among other places, this embodiment is intended as a non-limiting example of the principles of the present invention. It will be readily apparent to one skilled in the art, the range of applications suited to the principles of the present invention. The device described herein, as a non-limiting example, with minor adaptations to the object-holding element and choice of fluid coating materials, is well suited for a wide range of objects to which a coating is applied.

Figure 1:
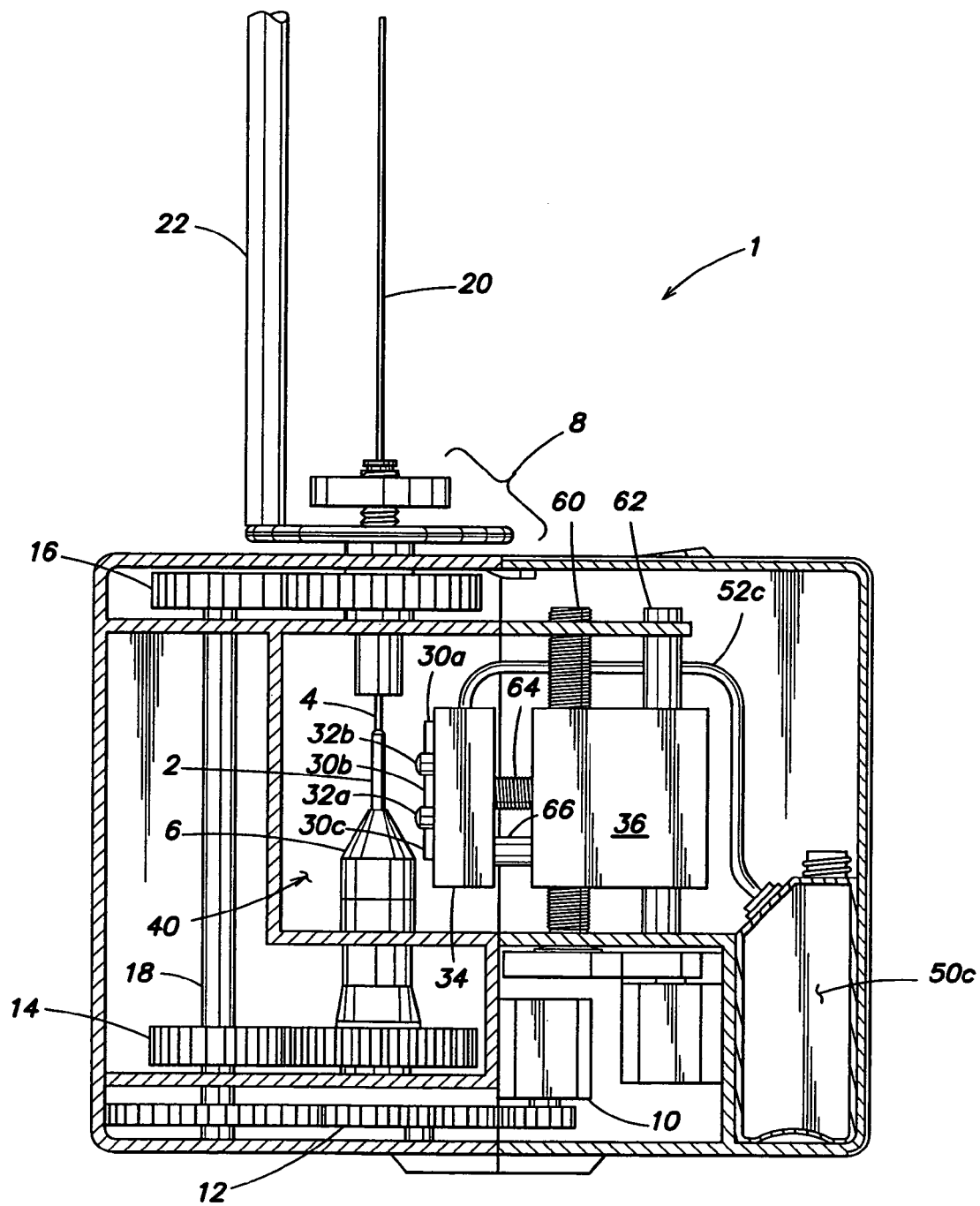
FIG. 1 is a cut-away side elevation of a stent coating device constructed and operative according to the teachings of the present invention.
Figure 2:
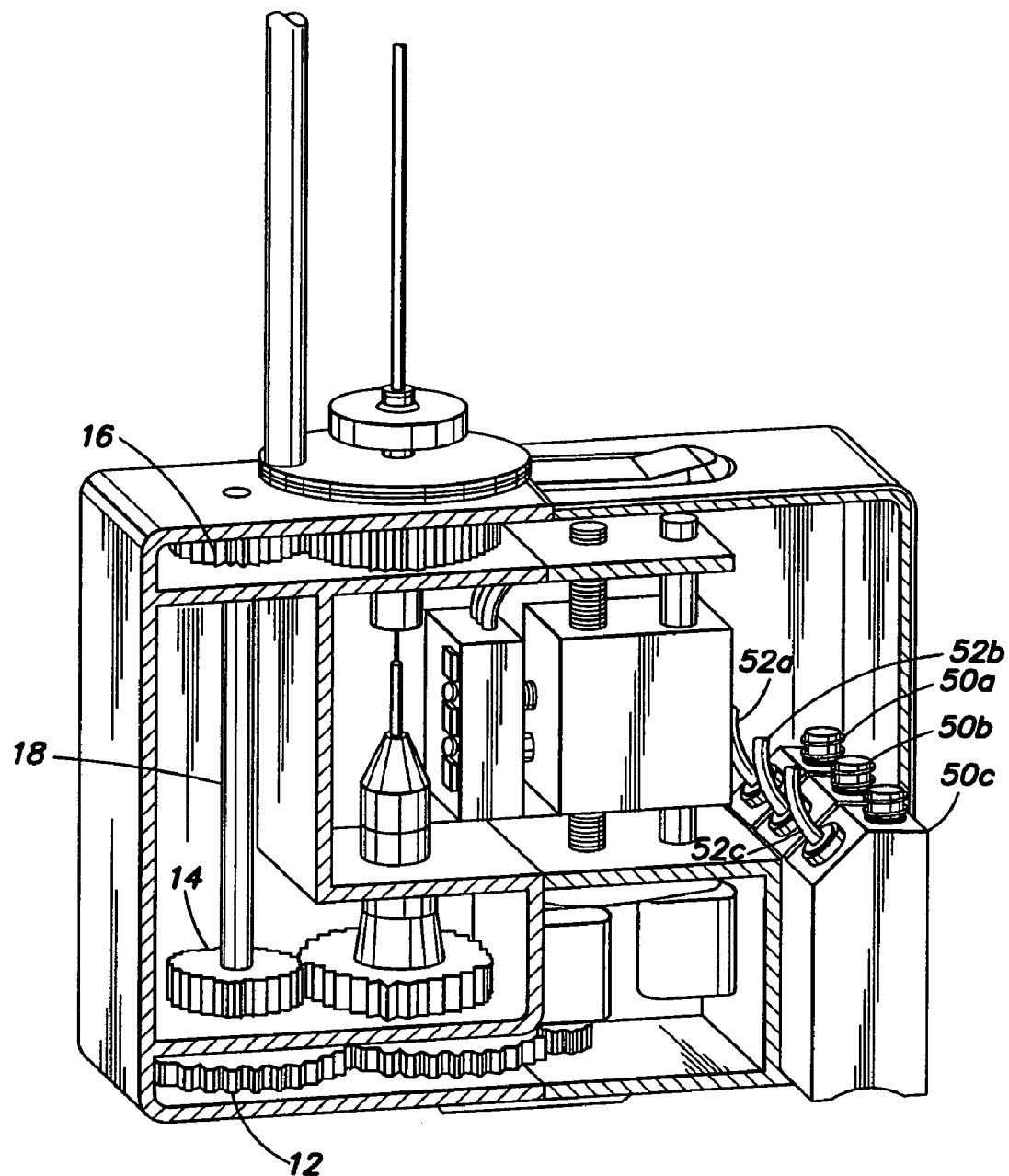
FIG. 2 is a cut-away perspective view of the stent coating device of FIG. 1.
Figure 6:
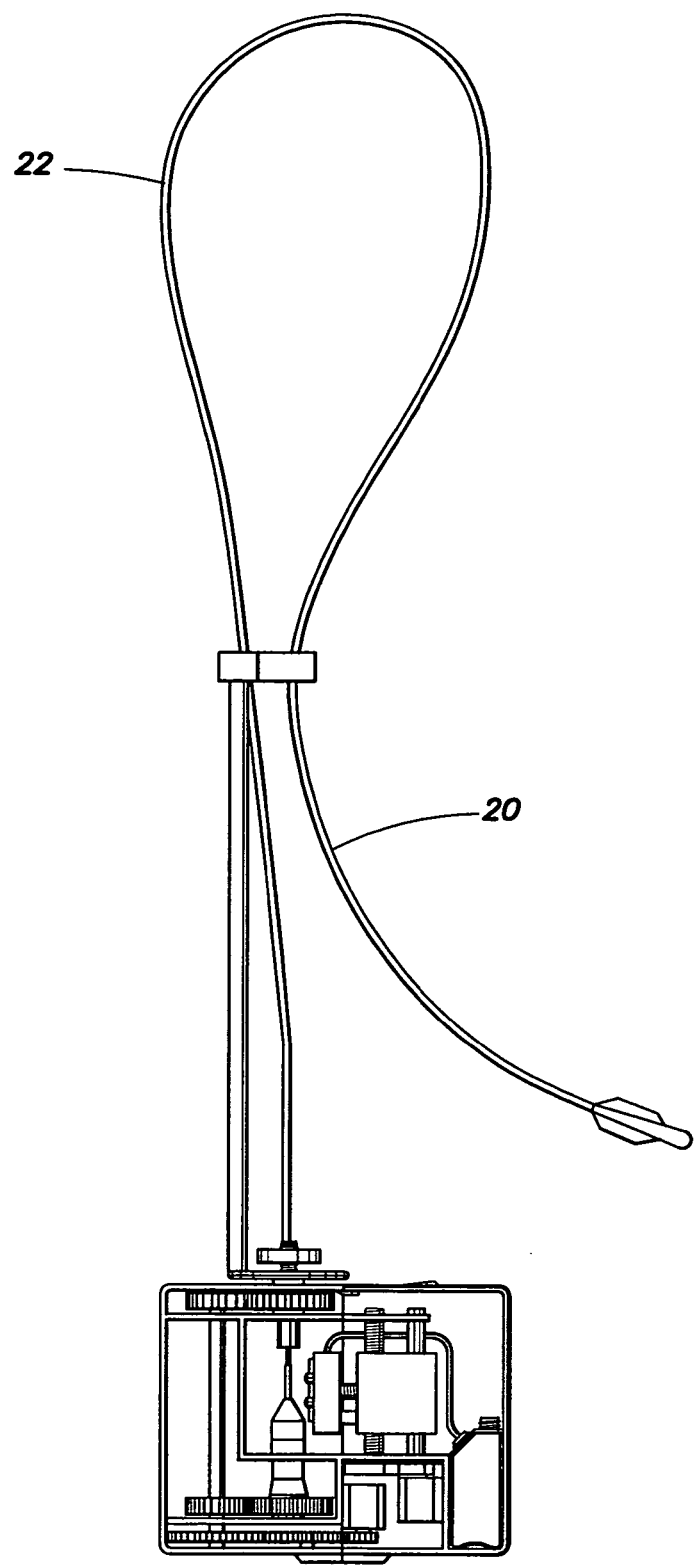
FIG. 6 is a side elevation of the stent coating device of FIG. 1 showing the full length of a catheter being supported by the support antenna.

Referring now to the drawings, FIG. 1 illustrates a device 1 for applying a coating to a stent 2 that is deployed on a catheter 4. The coating being applied may be a synthetic or biological, active or inactive agent. The perspective view of FIG. 2 is of the same side of the device as FIG. 1, and therefore when the description of elements of the device will be better understood, FIG. 2 will be referenced. The catheter 4 is placed in an application compartment 40 and held in position by a rotatable catheter-holding base 6 and a rotatable upper catheter-holding element 8, configured for substantially continued rotation, that is, they may complete a plurality of full 360° rotations, as required, during the coating process. The actual rotation may be substantially fully continuous (non-stop) or intermittent. The upper catheter-holding element will be discussed in detail below with regard to FIG. 4. The enclosed application compartment provides a sterile environment in which the coating process is performed. The rotation of the catheter-holding base and the upper catheter-holding element is actuated and synchronized by a motor and gear system that includes gear clusters 12, 14, 16, and shaft 18 (see also FIG. 2). Alternatively, the gears may be replaced by drive belts, drive chains or any other mechanism that will maintain a synchronized drive, for example, two DC servo motors driven in a master/slave mode by the system controller. The remaining length of the catheter is supported by a support antenna 22, as illustrated, by non-limiting example, in FIG. 6. As noted above, the object-holding elements may be modified so as to hold any object suitable for coating according to the teachings of the present invention.

The coating is applied by a drop-on-demand inkjet system in association with an optical scanning device 32 and processing unit. As the object is rotated by the object-holding element, the optical scanning device scans the surface of the object. The output from the scanning device is used by the processing unit to determine if the surface area currently aligned with the coating applicator is of the type of surface to be coated. When it is determined that the desired type of surface is aligned with the coating applicator, the processing unit activates the coating applicator and the coating is dispensed. The embodiment shown here includes three inkjet coating applicators 30a, 30b, and 30c, and two optical scanning devices 32a and 32b. The optical scanning devices may be configured to generate digital output or an analog signal, which is in turn analyzed by the processing unit. It should be noted that the number of coating applicators and scanning devices may be varied to meet design or application requirements.

The three coating applicators and the two optical scanning devices are mounted on a displaceable applicator head 34. The position of the applicator head 34 within the application compartment, and thereby the spatial relationship between the coating applicator and the stent, or other object being coated, is regulated by the application control module 36, which is, in turn, controlled by the processing unit. The change of position of the applicator head 34 is effected vertically by turning the vertical positioning screw 60 in conjunction with guide shaft 62, and horizontally by turning the horizontal positioning screw 64 in conjunction with guide shaft 66. The vertical repositioning in conjunction with the rotation of the object enables the coating applicator to traverse substantially the entire surface of the object requiring coating.

Fluid coating material is stored in three fluid reservoirs 50a, 50b, and 50c (see FIG. 2), and supplied to the respective coating applicators by the fluid supply hoses 52a, 52b and 52c (see FIG. 2). In general use, each of the fluid reservoirs contains a different coating material, thus, each coating applicator will deposit a different coating material on the stent or other objected being coated, as required. Further, a plurality of coats may be applied, each coat being of a different coating material and, if required, of a different thickness. Thus, at the time of coating, a single appropriate coating material may be chosen from the materials provided, or a combination of coatings may be chosen. It should be noted that while the fluid reservoirs are shown here in a compartment inside the device housing, this need not always be the case, and the reservoirs may be external to the housing.

Figure 3:
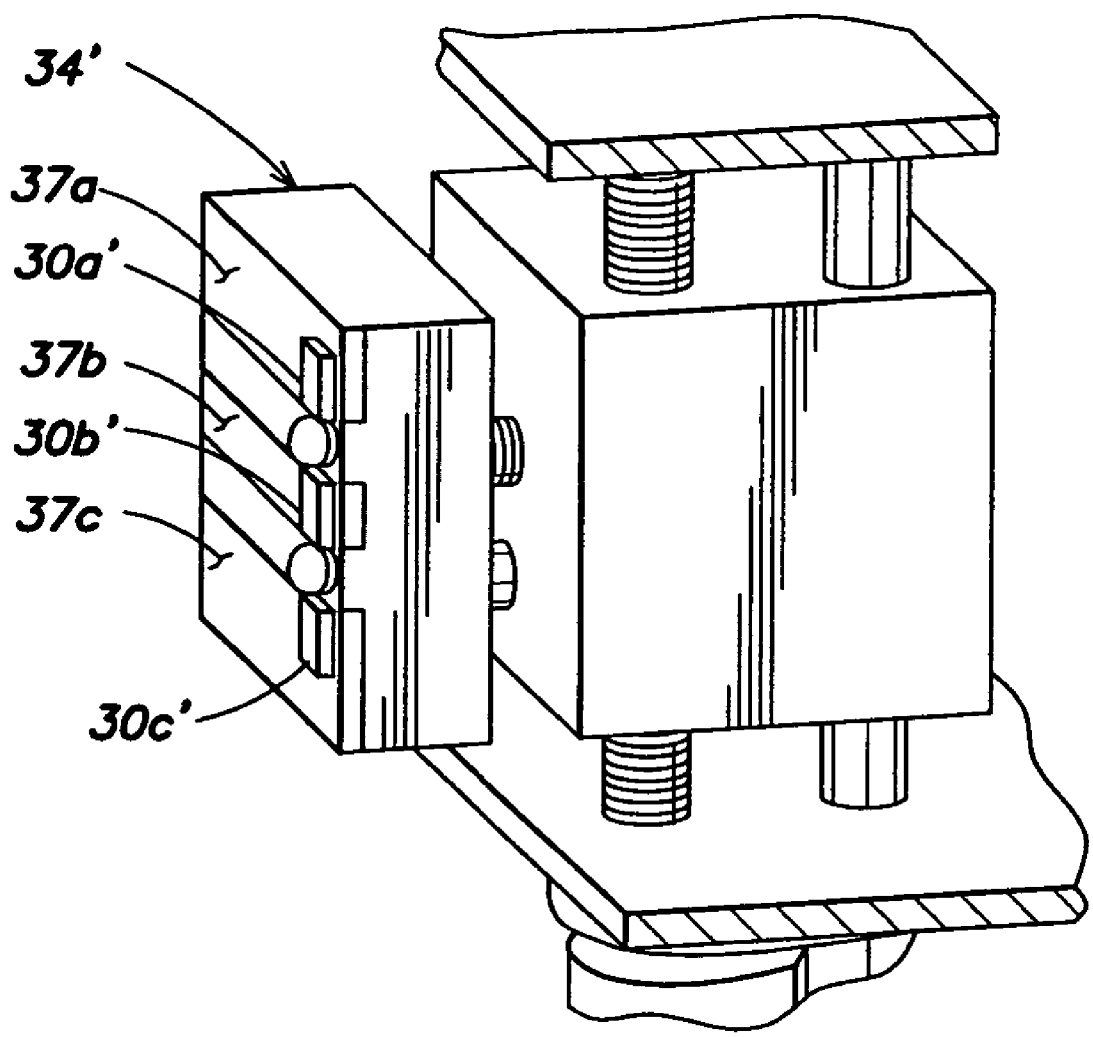
FIG. 3 is a perspective detail of an alternative displaceable applicator head constructed and operative according to the teachings of the present invention, shown here configure with disposable coating applicators.

It should be noted that, alternatively, the inkjet system may be deployed in a disposable housing that also includes a fluid reservoir filled with coating material. The fluid reservoir may be an enclosed volume that is integral to the disposable housing or it may be a coating filled cartridge that is inserted into a receiving cavity in the disposable housing. In this case, as illustrated in FIG. 3, a displaceable applicator head 34' is configured to accept one or more of disposable housings 37a, 37b and 37c, which in turn house disposable inkjet coating applicators 30a', 30b' and 30c', respectively. The fluid reservoirs (not shown) for each applicator are housed in that portion of the disposable housing that is deployed within the displaceable applicator head 34.

Figure 4:
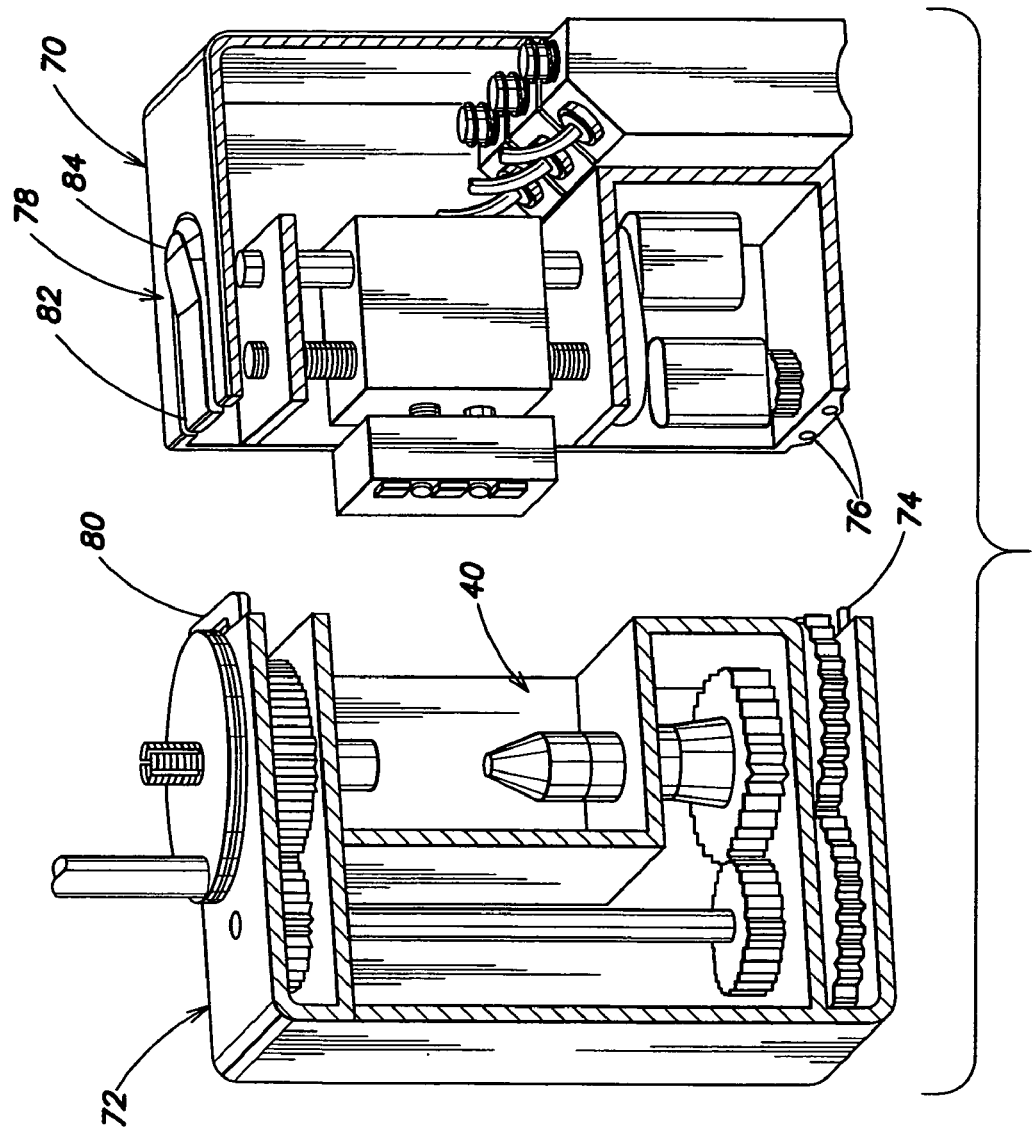
FIG. 4 is a cut-away perspective view of the stent coating device of FIG. 1, showing the detachable section of the housing separated from the base section of the housing.

FIG. 4 illustrates how the base housing section 70 and the detachable housing section 72 are interconnected. The two sections are held together by inserting pins 74, extending from the detachable housing section, into the corresponding holes 76, located in the base housing section, and engaging the latch mechanism 78 with the catch element 80. Detachment of the two sections is accomplished by pressing the release button 84, which raises the end 82 of the latch thereby releasing the catch element. The two sections are then pulled apart. The application compartment is defined by a top, floor and three walls located in the detachable housing section and one wall on the base housing section. The detachable housing section is configured to be disposable, or if desired, easily cleaned and re-sterilized.

Figure 5:
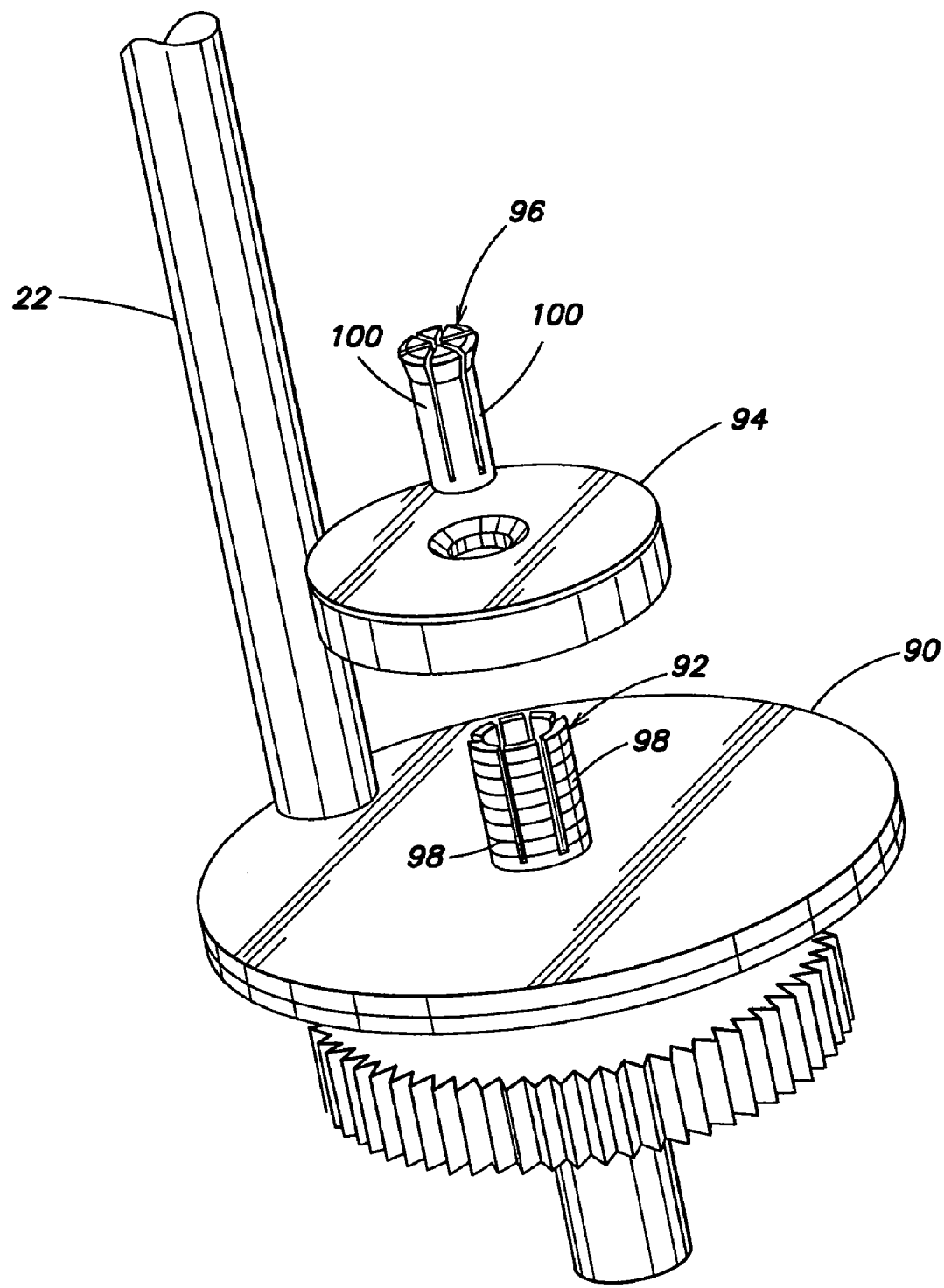
FIG. 5 is a perspective detail of an upper stent holding element, constructed and operative according to the teachings of the present invention.

The detail of FIG. 5 illustrates the components of the upper catheter-holding element. Extending from substantially the center of the rotating base plate 90, is a threaded tube 92. This tube 92 is the external end of the passageway through which the catheter tip with the stent attached is inserted in order to deploy the stent in the application compartment of the coating device. The tube is cut longitudinally several times, to create threaded sections 98, here six that are configured to flex outward from the center. The tightening-disk 94, has a correspondingly threaded center hole for deployment on the tube 92 such that when the tightening-disk is brought to a position proximal to the base plate, the threaded sections near the end of the tube will flex outwardly thereby enlarging the diameter of the opening. The gripping element 96 also has divergently flexing fingers 100. In operation, the gripping element is deployed around the catheter, which is then passed through the tube and into the application compartment. Once the catheter is positioned on the catheter holding base, the gripping element is at least partially inserted into the opening of the tube. The tightening-disk 94 is then rotated about the tube, and brought to a position proximal to the end of the tube, the outwardly flexing sections of the tube 98 are brought into an un-flexed state thereby decreasing the diameter of the opening. The decrease in the diameter of the tube opening pushes the fingers 100 of the gripping element against the catheter, thereby holding the catheter in place.

A non-limiting example of the stent coating process as accomplished by the above described device would be as follows:

1. The fluid reservoirs are filled with the required fluid coating materials.

2. The parameters of the coating are inputted into the processing unit. The parameters may include, by non-limiting example, the coating material to be applied, the thickness of the coating, number of multiple layers of different coating material, the order in which the layered materials are to be applied, and the thickness of each layer. The parameters may be determined by the physician at the time the coating is applied or the parameters may be pre-set, such as those determined by medical regulations. In the case of pre-set parameters, the physician would simply input a "start" command.

3. The catheter is positioned in the application compartment and the upper catheter-holding element is tightened.

4. As the catheter rotates, the optical scanning device scans the surface of the catheter to distinguish between the surface of the balloon and the surface of the stent.

5. When a portion of the surface of the stent is detected and determined to be in alignment with the appropriate coating applicator, the processing unit selectively activates the applicator, thereby ejecting the necessary amount of coating material, which is deposited substantially only on the surface of the stent.

6. Throughout the coating process, the position of the applicator head is adjusted as required. This adjustment may bring the coating applicator closer to, or farther away from, the surface of the stent, and it may adjust the vertical deployment of the coating applicator, thereby allowing different areas of the surface of the stent to be coated. Further, if a different fluid coating material is needed for a different layer of the coating, the coating applicator for that particular coating material may be brought into appropriate alignment for deposition of the new coating material on the stent.

7. When the coating process is completed, the catheter with the now coated stent is removed from the device, and the stent is ready for implantation.

8. The detachable housing section is removed and may be cleaned and sterilized for re-use, or simply discarded.

It should be noted that in some cases it may be desirable to coat substantially the entire surface of the object being coated. This may be accomplished in at least two ways. The object itself may have only one type of surface. Alternatively, the scanning device may be configured so as to provide adjustable scanning sensitivity. In the latter case, the sensitivity of the scanning device may be adjusted such that the output is indicative of only one type of surface and the processing unit is unable to distinguish between different types of surfaces.

Figure 7A:
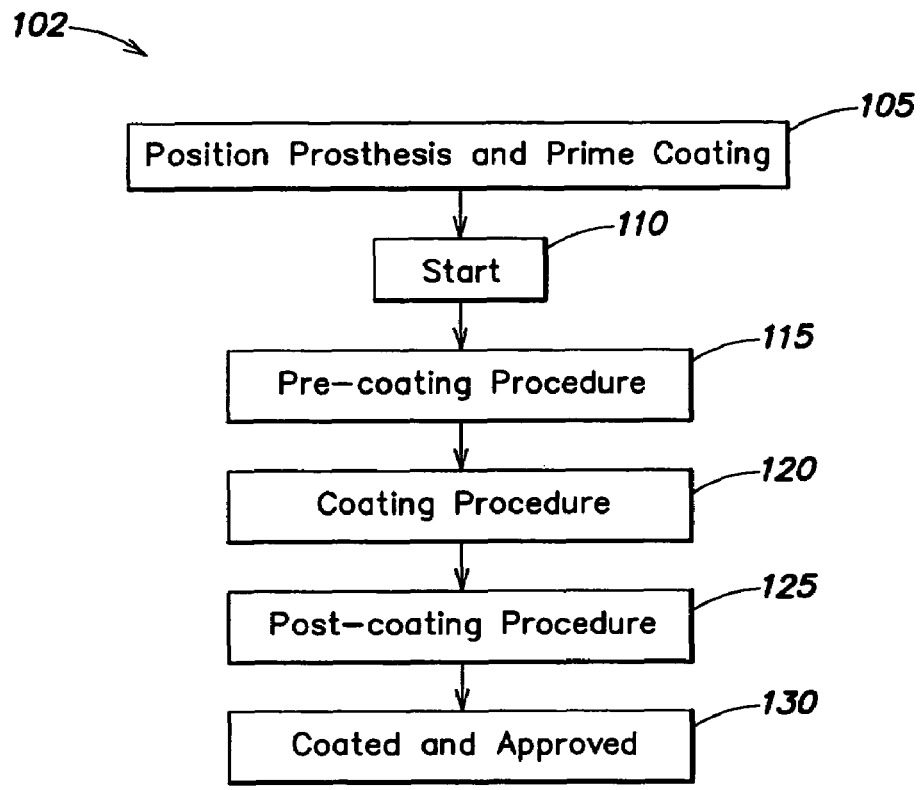
FIG. 7A is a flow chart of a non-limiting embodiment of a method for coating a stent according to the present invention.

The flowchart of FIG. 7A illustrates a process for coating a prosthesis 102 based on the present invention. In this non-limiting example, the prosthesis is a stent that is to be coated with a therapeutic agent. A first step 105 is to place the stent and therapeutic agent container in the stent coating device. The system is then ready for processing the stent. The system starts at step 110. A pre-coating procedure 115 collects information in the processing unit (not shown) of the stent coating device to be used during a coating procedure 120. A post-coating procedure 125 verifies that the stent has been properly coated and should be approved for removal 130.

Figure 7B:
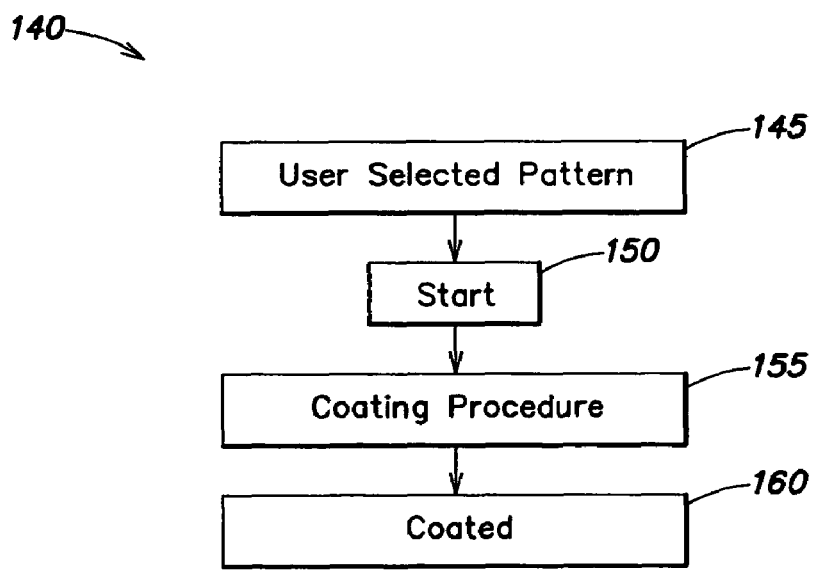
FIG. 7B is a flow chart of the method known in the art for coating a stent.

The flowchart of FIG. 7B illustrates the process for coating stents 140 known in the art. The user selects a pattern 145 according to the type of stent to be coated and the pattern of coating to be delivered. The pattern selected varies on parameters provided by the stent manufacturer and the coating to be applied. The process starts 150 according to the pattern that has been selected. The coating procedure 155 applies the coating to the stent, and once complete, the coated stent 160 is ready for removal.

Figure 8:
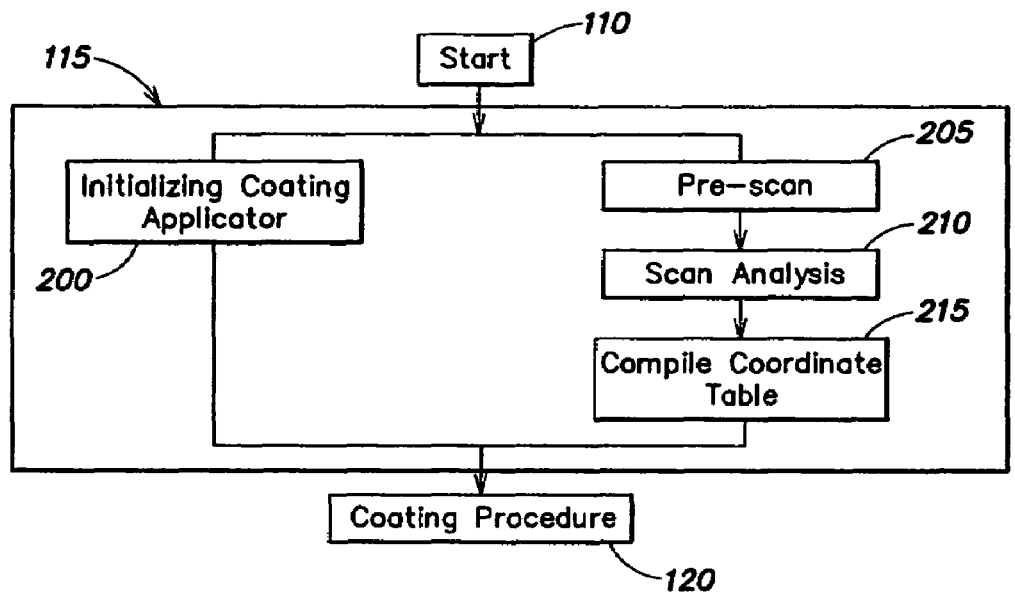
FIG. 8 is a flow chart of a non-limiting embodiment of the pre-coating procedure according to the present invention.

FIG. 8 illustrates the pre-scanning procedure 115. The stent is pre-scanned 205 prior to the coating procedure 120. In parallel, the application control module is initialized 200. Initialization of the application control module comprises finding a specific point on the stent to begin coating. The pre-scan is analyzed 210 in the processing unit. The analysis determines and compiles the coating coordinates table 215 to be used to position the application control module.

There is, often times, a large deviation even between stents of the same design, after the stent is crimped on the balloon catheter. Crimping does not always result in a uniform deformation of the stent structure and, as a result, some portions of the stent may be more densely packed than other portions. Some intersections of stent struts may have different angles of incidence. The preprogrammed pattern is not helpful to manage these deviations from the design. Pre-scanning can provide a check for defects in the stent structure prior to coating and can also provide the best positions on which to spray the coating. Pre-scanning can also provide the optimal path to follow over the stent surface to be coated. In some applications, only a portion of the stent is to be coated and pre-scanning can prevent over-jetting of the coating on a specific location. Over-jetting, otherwise, can result in coating landing on the balloon catheter.

Scanning can be achieved by a variety of imaging techniques known in the art of imaging, including but not limited to, photographic, video, infrared, and VCSEL (Vertical Cavity Surface Emitting Laser) technologies using a variety of detectors. AVCSELs can be used as the detector for optical imaging, and can double as the applicator itself. Choquette, Kent D., *Vertical Cavity Surface Emitting Lasers-Light for Information Age*, MRS Bulletin, pp. 507-511, July 2002. In one non-limiting embodiment, a photograph of the stent is taken by a detector. The stent is rotated slightly (e.g., one-half to a few degrees) and then another photograph is taken, resulting in at least several dozen photographs total. The detector is focused sufficiently close to the stent to record enough resolution relative to the coating droplet to be applied. If the stent is long, the rotation may have to be repeated to capture the top and bottom of the stent.

A light source can be positioned on the same side as the detector or on the opposite side of the detector relative to the stent. In the embodiment where the light source is on the same side as the detector, the detector receives light reflected by the stent. The stent appears light in color and the balloon appears dark in color. In the embodiment where the light source is on the opposite side of the detector, the detector receives light transmitted through the balloon and around the stent struts. The stent appears dark in color and the balloon appears light in color. The contrast between the light and dark color in both embodiments can be used for edge analysis. Edge analysis comprises determining the edges of the stent and finding the center-line of stent surface to be coated. The edges and center-line determine the coating coordinates which are collected for each surface of the stent to be coated in the coating coordinates table.

In one non-limiting embodiment, the pre-scan is compared to an index of patterns in the processing unit. This can be used to confirm the accuracy of the edge analysis and provide a safety measure for detection of defects in the stent or errors in the edge analysis.

Figure 27:
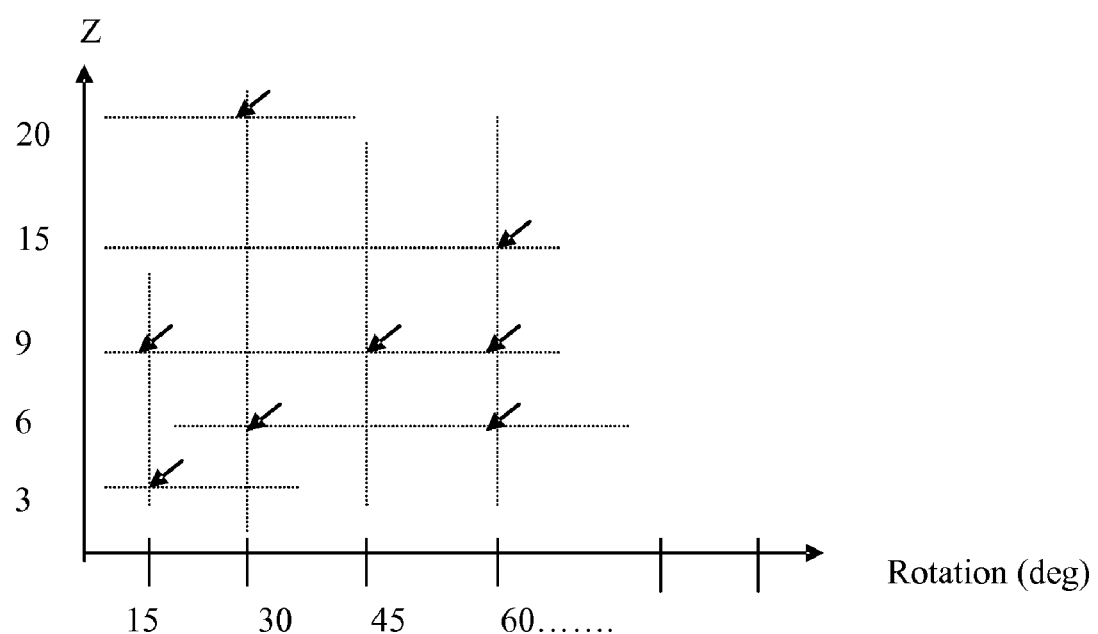
FIG. 27 is a mapping of coordinates where coating is applied as a function of distance along the device and the relative axial rotation.

Coating coordinates can be interpreted and coded as raster or vector type of data forms. These data forms describe different translation of the applicator by the Z driver. Both data forms comprise using an algorithm to find all the coordinates of the stent that should be coated and compiling a map of "to be coated points" or coordinates. FIG. 27 illustrates a map of coordinates showing the point location on Z, R as a function of the relative axial rotation R in degrees or radians.

Vector type coating comprises taking the unique variables (e.g., Z and R, rotation), and using another algorithm to select the shortest distance or otherwise most efficient path to move between one coating coordinate and the next most proximate coordinate to be coated. Vector coating can also comprise creating a list of coordinates in sequential order. Table 1 illustrates a "best pass algorithm" as a coordinate table correlating location on Z to angle of rotation R for each coordinate.

TABLE 1

| Coordinate no. | Z | Rotation R |
|---|---|---|
| 1 | 3 | 15 |
| 2 | 6 | 30 |
| 3 | 9 | 45 |
| 4 | 6 | 60 |
| 5 | 9 | 60 |
| 6 | 15 | 60 |

Control software in the processing unit can calculate a set of movement vectors for the application control module between each set of sequential coordinates. Vector parameters may comprise coordinates, $\Delta z$ (change in location between two adjacent points or coordinates on Z axis), $\Delta rot$ (change in angle between coordinates), velocity between the coordinates, etc. Table 2 illustrates vectors that can be calculated from coordinate table in Table 1. Each vector can have a different velocity associated with it represented as values a, b, and c. Each vector can have a difference quantity associated with it represented as values d, e, f, g, h which may be the same or different. Other parameters can also be associated with each vector.

TABLE 2

| Vector | $\Delta z$ | $\Delta rot$ | Velocity | Quantity |
|---|---|---|---|---|
| 1-2 | 3 | 15 | a | d |
| 2-3 | 3 | 15 | a | e |
| 3-4 | −3 | 15 | a | f |
| 4-5 | 3 | 0 | b | g |
| 5-6 | 6 | 0 | c | h |

A raster type coating comprises using an algorithm to find all the coordinates of the stent that should be coated and compiling a map of coordinates. This is similar to vector type coating as is illustrated in FIG. 27. Raster type coating, however, also comprises taking the unique variables (e.g., Z and rotation), and using a different algorithm to calculate and compile a coordinate table of Z coordinates for each rotation angle in predetermined increments of rotation. The term "rotation resolution" refers to the number of increments in rotation angle. Raster type coating is rotation-resolution-specific. This means that raster printing is calculated and executed at one specific rotation resolution, or in a variety of other manipulations inter-relating the prosthetic item to be coated, the holder for such prosthetic and the applicator nozzle. Table 3 illustrates a coordinate table correlating angle of rotation with locations on Z. These locations: Z1, Z2, Z3, Z4, etc. represent intersections with the surface of the stent to be coated at each angle of rotation.

TABLE 3

| ROTATION ANGLE R | Z1 | Z2 | Z3 | Z4 |
|---|---|---|---|---|
| 15 | 3 | 9 | | |
| 30 | 6 | 20 | | |
| 45 | 9 | | | |
| 60 | 6 | 9 | 15 | |

Control software in the processing unit can calculate the Z coordinates for each angular position and direct the application control module and coating applicator to go to an angular rotation position and move along Z at a regulated, constant or variable velocity. While moving along Z, the coating applicator injects at Z1, Z2, Z3, Z4, etc. After traveling the full length of the stent along Z, the application control module moves the coating applicator to the next angle of rotation, changes the direction along Z (now opposite the previous direction) which the coating applicator travels. While traveling in this new direction, the coating applicator injects over the next Z locations.

Additional raster-based manipulations could include, for example, rotational movements of the stent in conjunction with serial, stepped Z-axis movements, or "screw-like" movements along a helical path of the stent accomplished by simultaneous movement of rotation and stepped Z-axis movements, as is described below. In any event, the raster-based coating process results in motion with respect to the stent and applicator that covers the entire prosthetic, while the vector-based coating process only travels over the "to be coated" surfaces. Consequently, the vector-based approach is object dependent, while the raster-based approach is system defined.

Figure 11A:
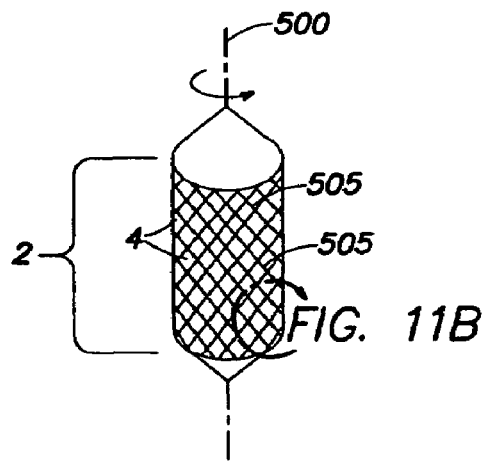
FIG. 11 illustrates a detail of a stent on a balloon catheter, and a blowup perspective of the stent surface to be coated.
Figure 11B:
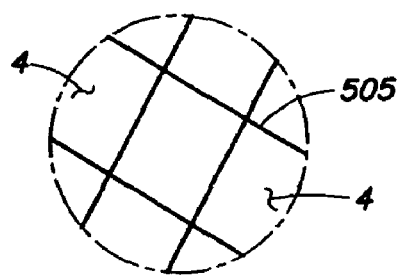

FIG. 11 illustrates a stent 2 on a balloon catheter 4. An axis of rotation 500, is also the axis of symmetry 500 for the stent. The magnified window of FIG. 11 shows the stent structure to be coated 505 and gaps in stent structure where balloon catheter 4 is not covered by the stent. During scanning, the stent is rotated in incremental angles according to the rotation resolution to generate the coordinate table. During coating, the application control module rotates the stent in different, usually smaller and, therefore, more dense, incremental angles and positions the coating applicator at the Z,R locations to coat the stent. In one non-limiting embodiment, the coating applicator can drop-on-demand a coating with accuracy as is known in the art of ink-jet printing.

Figure 9A:
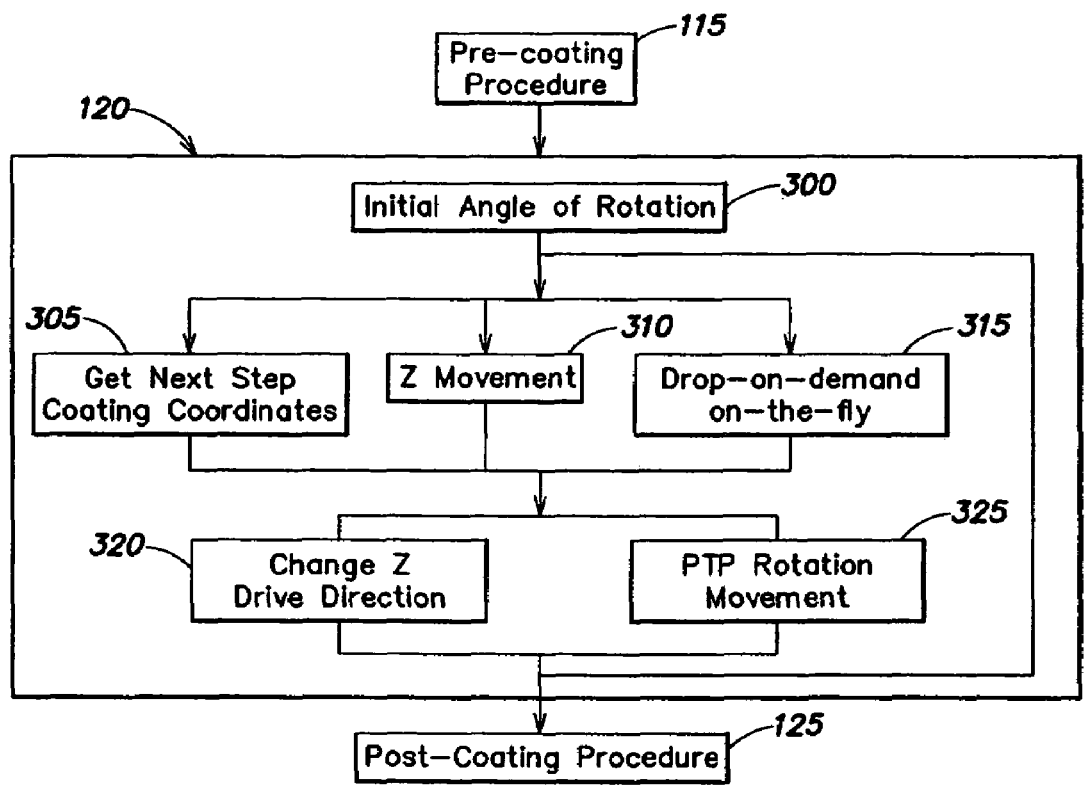
FIG. 9A is a flow chart of a non-limiting embodiment of the coating procedure according to the present invention.

The flowchart of FIG. 9A illustrates an embodiment of the coating procedure 120. The present embodiment contemplates raster coating accomplished by longitudinal movement of the applicator along the length of a cylindrical body and point-to-point ("PTP") rotation of the cylindrical body or applicator around the circumference of the cylindrical body. An initial angle of rotation is selected 300. The application control module moves the coating along the Z axis 310, while controlling drop-on-demand at Z coordinate 315, and receiving the next coating coordinate from the processing unit 305. Once the coating applicator has moved along the length of the stent, the application control module changes the direction of travel along the Z axis of the coating applicator 320, and rotates the stent to the next angle of rotation 325. This process is repeated by repeating steps 310-325 until the stent has been coated according to the coordinate table. In one non-limiting embodiment, the change in incremental angle of rotation can be one-half of one degree and can require up to 500 rotations of the stent to coat each point in the coordinate table. Multiple coatings can be applied sequentially or simultaneously by repeating the steps and/or changing the coating reservoir.

In another embodiment, raster coating can be accomplished by coating along the circumferential rotation of the cylindrical body or applicator with PTP longitudinal movement of the applicator along the length of the cylindrical body. In another embodiment, raster coating can be accomplished by both circumferential rotation of the cylindrical body or applicator and longitudinal movement of the applicator with PTP longitudinal movement of the applicator or PTP rotation of the cylindrical body or applicator along the circumference of the cylindrical body. This embodiment results in a spiral, helical or "screw" type predetermined path.

In other embodiments, raster coating can be accomplished by following a predetermined path to apply coating material at desired locations of the prosthesis without regard to the pattern of the coating. In some embodiments, this predetermined path can incorporate the overall contour or geometrical shape of the prosthesis to efficiently cover the surface area which includes the desired locations to be coated. In some certain embodiments, efficiency can be realized by utilizing axes of symmetry or other geometrical simplifications of the overall contour of the prosthesis.

Figure 9C:
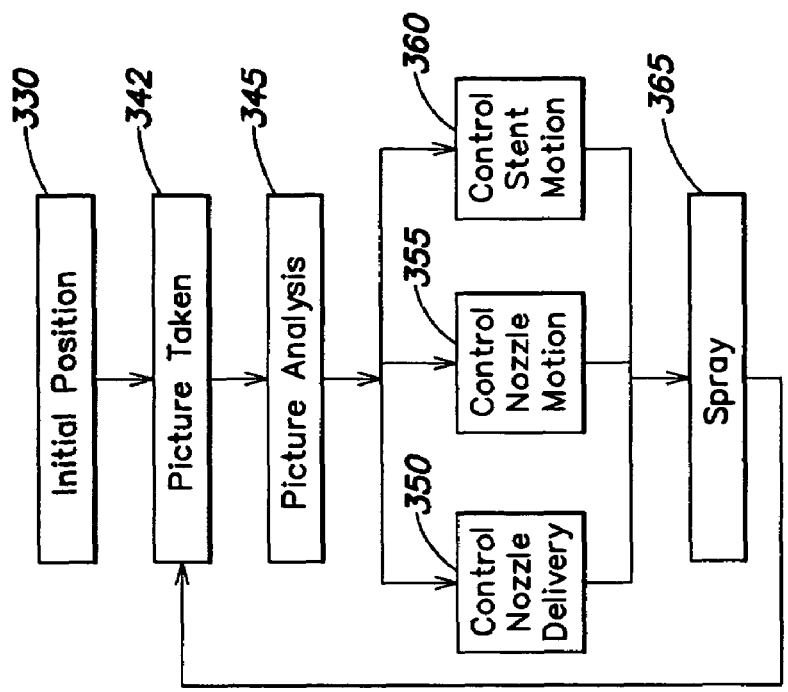
FIG. 9C is a flow chart of a procedure for coating a stent using real-time imaging.
Figure 9B:
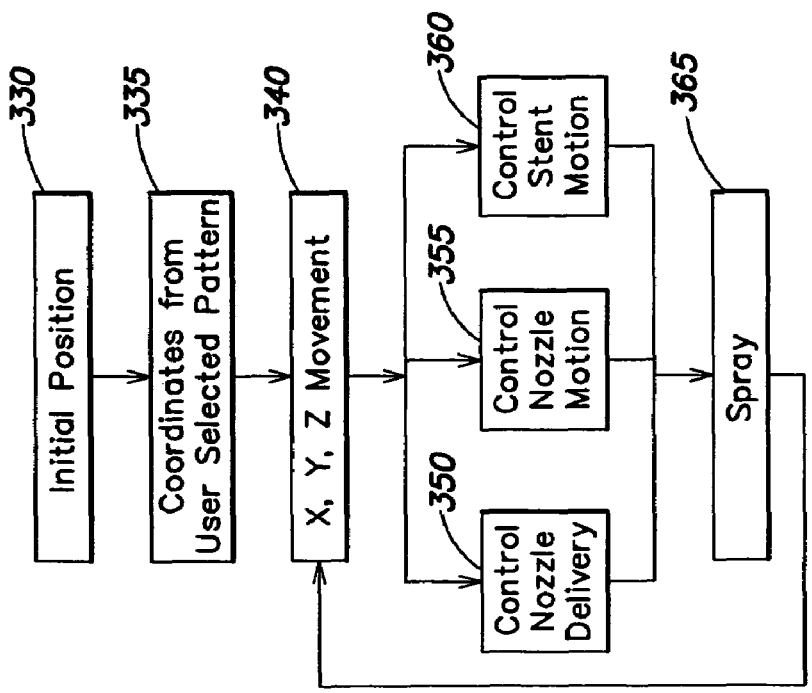
FIG. 9B is a flow chart of a procedure for coating a stent using a pre-selected library.

The flowchart of FIG. 9B illustrates the coating procedure 155 which is known in the art. The coating nozzle is in an initial position 330. The controller receives coordinates from a user selected pattern 335. The controller interprets the coordinates into X, Y, and Z constant velocity movement 340, and positions the nozzle to jet by controlling the nozzle delivery 350, the nozzle motion 355, and/or the stent motion 360. The nozzle then drops-on-demand 365. Then the nozzle travels over the stent to the next coordinate based on the user selected pattern.

The flowchart of FIG. 9C illustrates the coating procedure 155 which is known in the art also begins with the coating nozzle at an initial position 330. A picture of the nozzle, stent, and/or coating is taken 342. The picture is analyzed using vision software 345. The controller interprets the picture and positions the nozzle to jet by controlling the nozzle delivery 350, the nozzle motion 355, and/or the stent motion 360. The nozzle then drops-on-demand 365. This requires real-time imaging and adjustment prior to coating portions of the stent.

Figure 10:
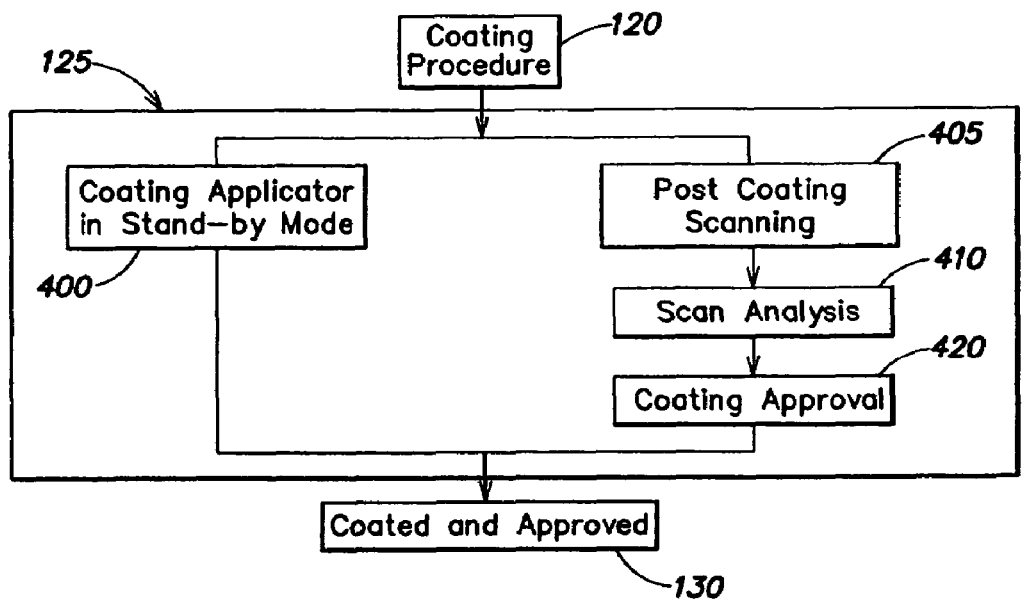
FIG. 10 is a flow chart of a non-limiting embodiment of the post-coating procedure according to the present invention.

The flowchart in FIG. 10 illustrates an embodiment of the present invention including a post-coating procedure 125. The coating applicator is held in stand-by mode 400, while the stent is post-scanned 405. Scan analysis 410 analyzes the coated stent for mistakes in coating and provides coating quality assurance and approval 420. If approved, the stent coating is complete 130. In one non-limiting embodiment, the coating comprises pigment to facilitate scan analysis by differentiating between the stent and coating. In one non-limiting embodiment, the pre-scan images can be used for the approval of the stent. Post-scanning facilitates locating coordinates where coating was not applied because of jetting problems. Post-scanning also facilitates in locating leakage or "overspray" points where the coating has leaked from the stent onto the balloon catheter.

Figure 12:
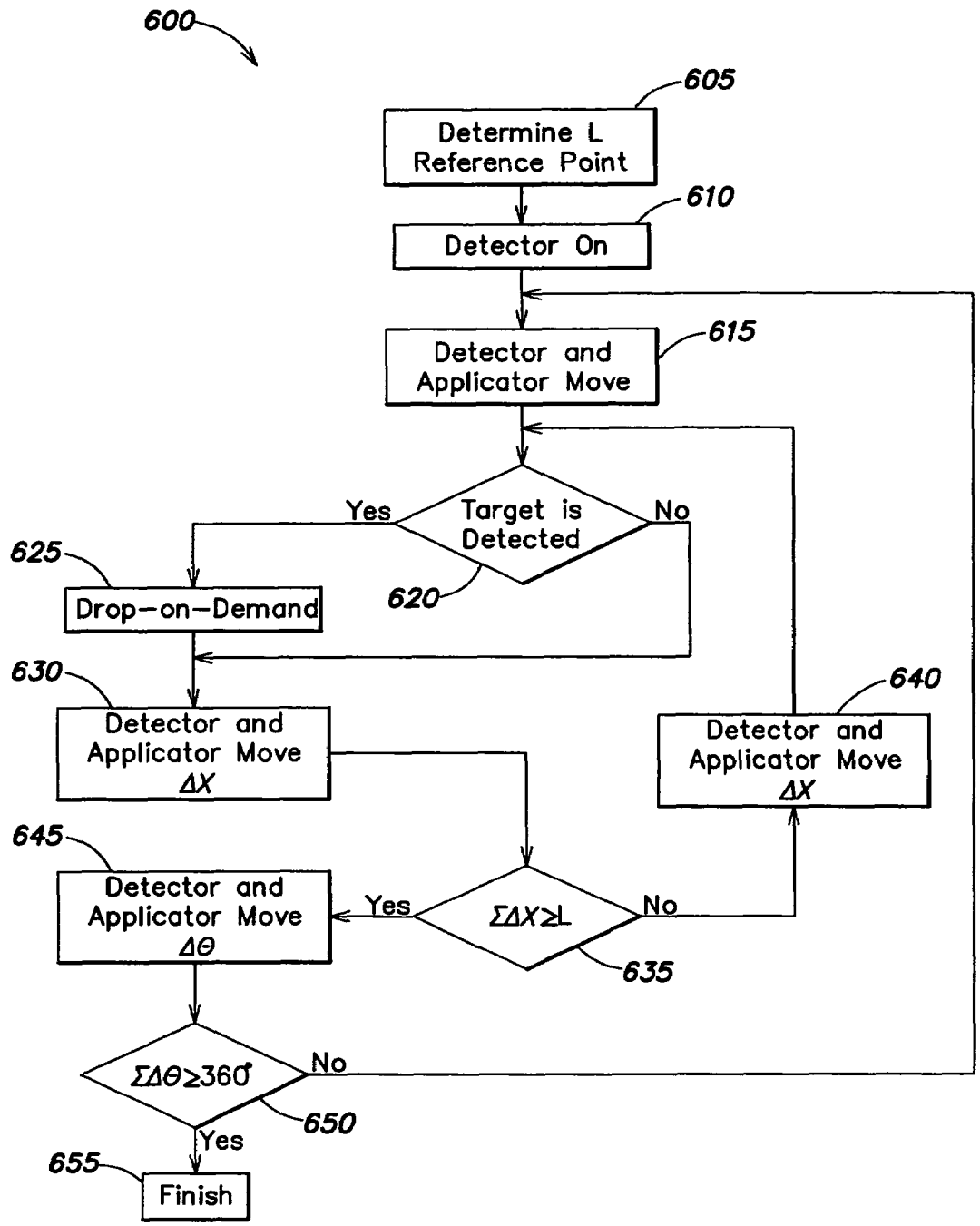
FIG. 12 illustrates a flow chart of a non-limiting embodiment of raster coating without the use of pre-scanning or post-scanning.
Figure 13:
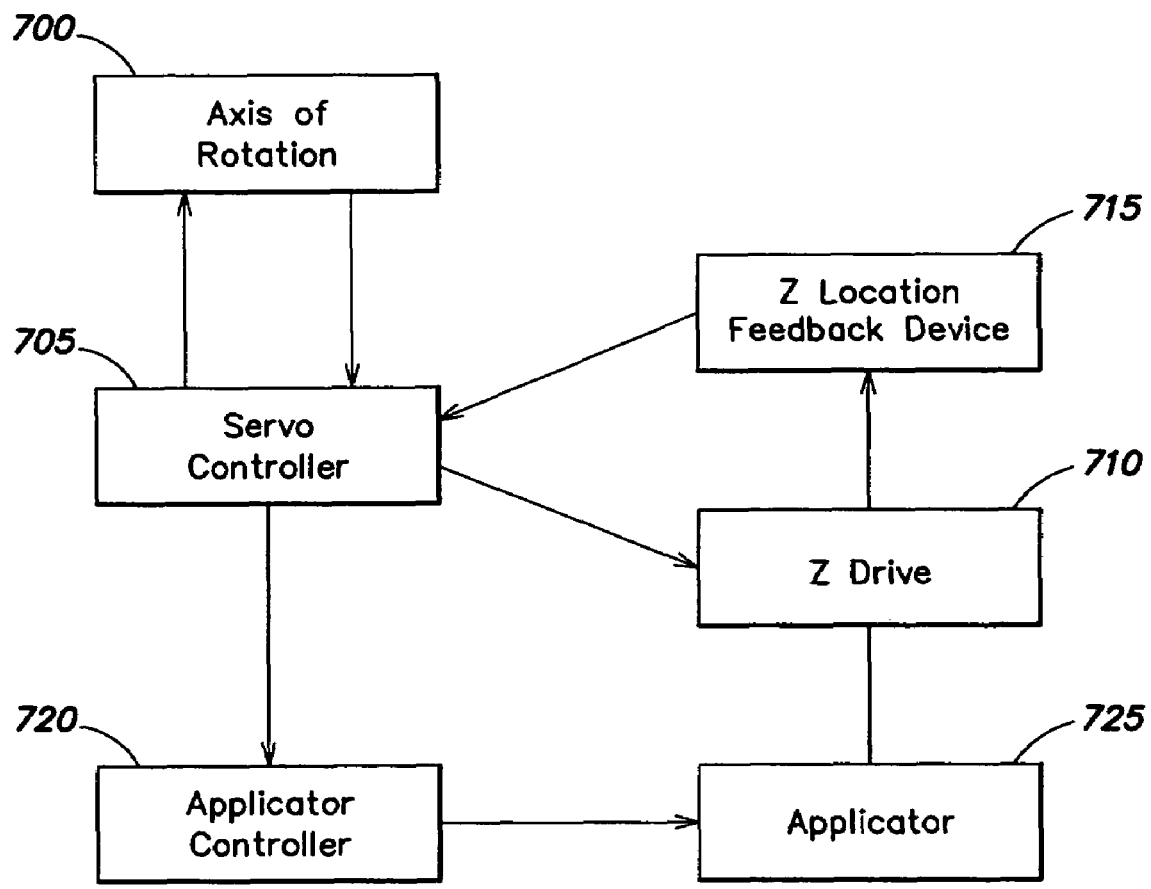
FIG. 13 illustrates a flow chart of an embodiment of "on-the-fly" translation of the applicator and delivery of the coating material. In alternative embodiments, the servo controller 705, Z drive 710, and Z location feedback device 715 can be all be bundled into the application controller 720.

The flow chart in FIG. 12 illustrates an embodiment of raster coating without pre-scanning or post-scanning. The method for coating a prosthesis 600, begins with setting 605 the predetermined length L, incremental linear movement Δx, and incremental angular movement Δθ, along with a reference point recognized as a characteristic feature of the prosthesis. The detector is turned on 610 and the detector and applicator move 615 linearly from the reference point an incremental distance Δx and Δθ along L. The detector looks for targets 620 as desired locations on the prosthesis to be coated. If the detector finds a target, the applicator drops-on-demand 625. If the detector does not find a target or after the applicator drops-on-demand 625, the detector and applicator move Δx 630. The detector determines whether it has traveled the full length L of the prosthesis 635 by determining whether the sum of the Δx movements is greater than or equal to length L (ΣΔx≧L). If the detector has not traveled the full length L, then the detector and applicator move Δx 640 and look for a target 620. If the detector has traveled the full length L, then the detector and applicator move Δθ 645. The detector determines whether it has traveled around the entire contour of the prosthesis 650 by determining whether the sum of the Δθ movements is greater than or equal to 360 degrees (ΣΔθ≧360°). If the detector has not traveled 360 degrees, then the detector and applicator move 615 linearly an incremental distance Δx and Δθ along length L. If the detector has traveled 360 degrees, then the coating is finished 655.

Figure 14:
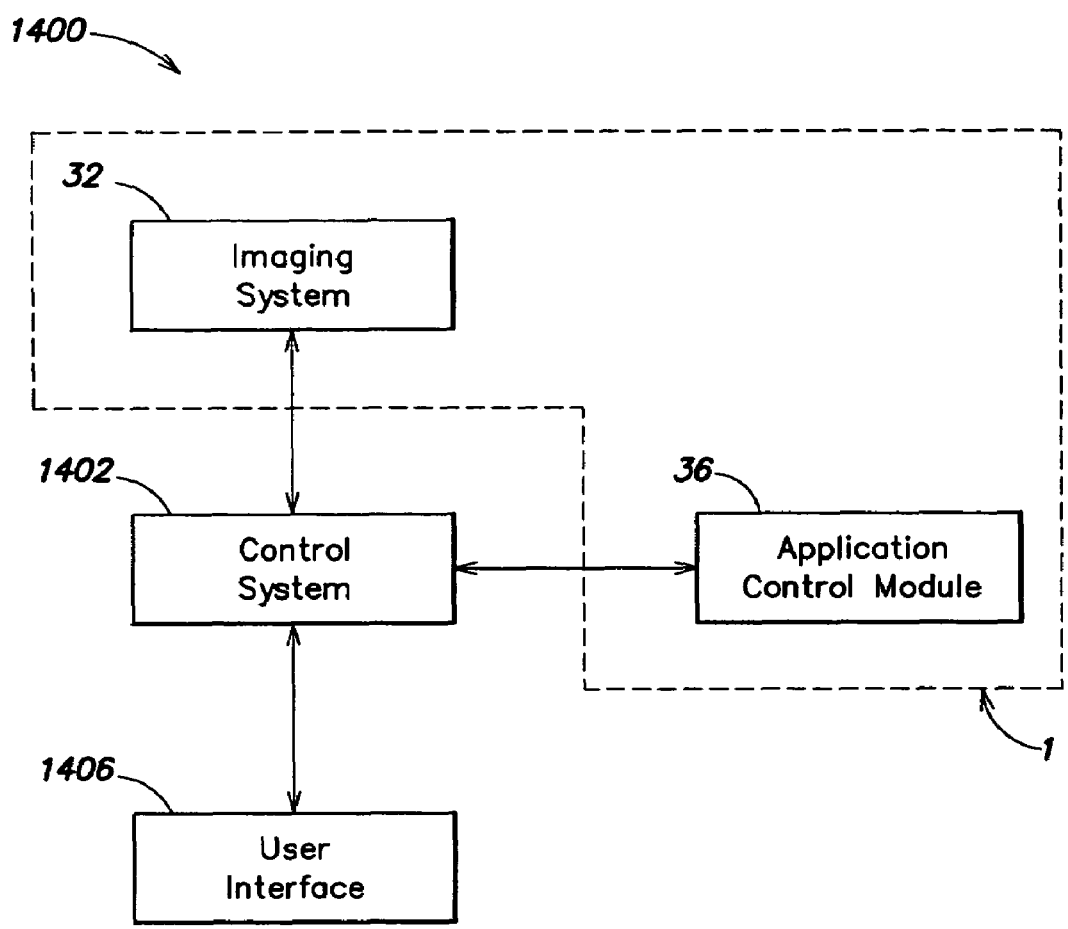
FIG. 14 is a functional block diagram of one embodiment of the present invention.

In another embodiment of the present invention, as shown in FIG. 14, a system 1400 includes a control system 1402 coupled to the device 1, (see FIG. 1) including the imaging system 32 and the coating application control module 36, previously described. In addition, the control system 1402 is coupled to a user interface 1406 to allow a user to input user selectable attributes of the system, e.g., material type, drop size, drop velocity, total volume to deposit, temperature of material, etc., in addition to being able to monitor operation of the system and receive alerts indicating how the process is functioning. The user interface 1406 may present this information via a display device such as a computer monitor and may use a graphical user interface as is known in the art.

The device 1 is coupled to the control system 1402 and incorporates the drop-on-demand applicator described above to place the coating on to the medical device. The device 1, in one embodiment of the present invention, is sized to fit on a desktop.

The control system 1402, in one embodiment of the present invention, is a general purpose personal computer or computing device implementing one or more application programs to control and interact with the imaging system 32, the user interface 1406 and the application control module 36. The computer may run an operating system as is known, such as, Microsoft Windows, UNIX, Linux or AppleOS. The application programs may be a combination of commercially-available programs or programs written in any one of a number of available programming languages including, but not limited to, C, C++, Java, Perl, and Fortran.

Figure 15:
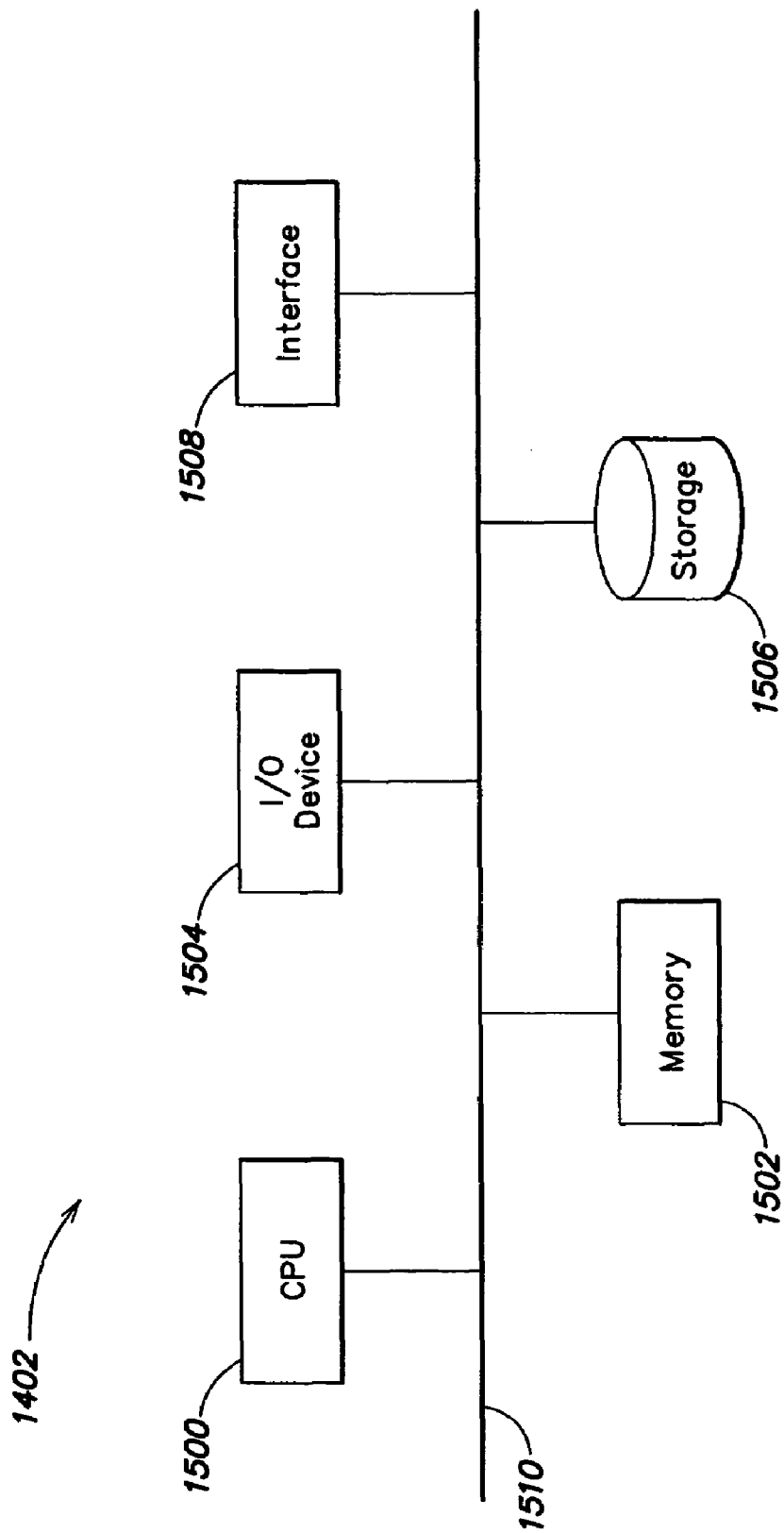
FIG. 15 is a block diagram of a computing device.
Figure 16:
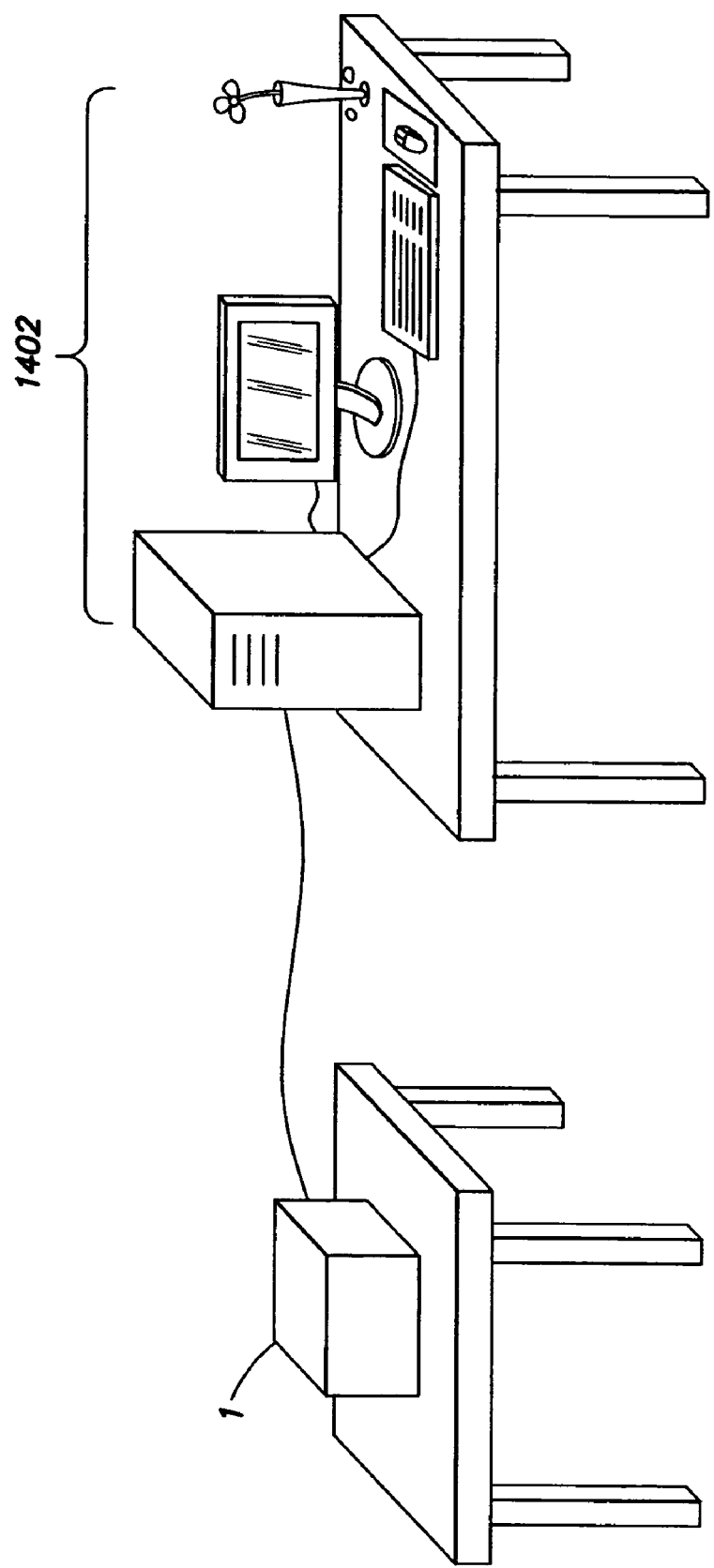
FIG. 16 is a diagram of one embodiment of the present invention.

The computer, as above, can be any one of a number of devices, however, these devices have some components and/or functionality in common, irrespective of their relative technical complexities. As shown in FIG. 15, a computing device includes a central processing unit 1500, a memory 1502, an input/output device 1504, for example, a keyboard, key pad or touch screen, storage 1506, for example, a hard disk drive, and an interface 1508 for communicating to a network. A bus 1510 couples these devices to one another to allow communication between them. As described above, the coating device 1 may be sized to fit on a desktop or laboratory bench in a clean-room or appropriately sterile environment. As shown in FIG. 16, the control system 1402 would be coupled to the coating applicator 1.

Figure 17:
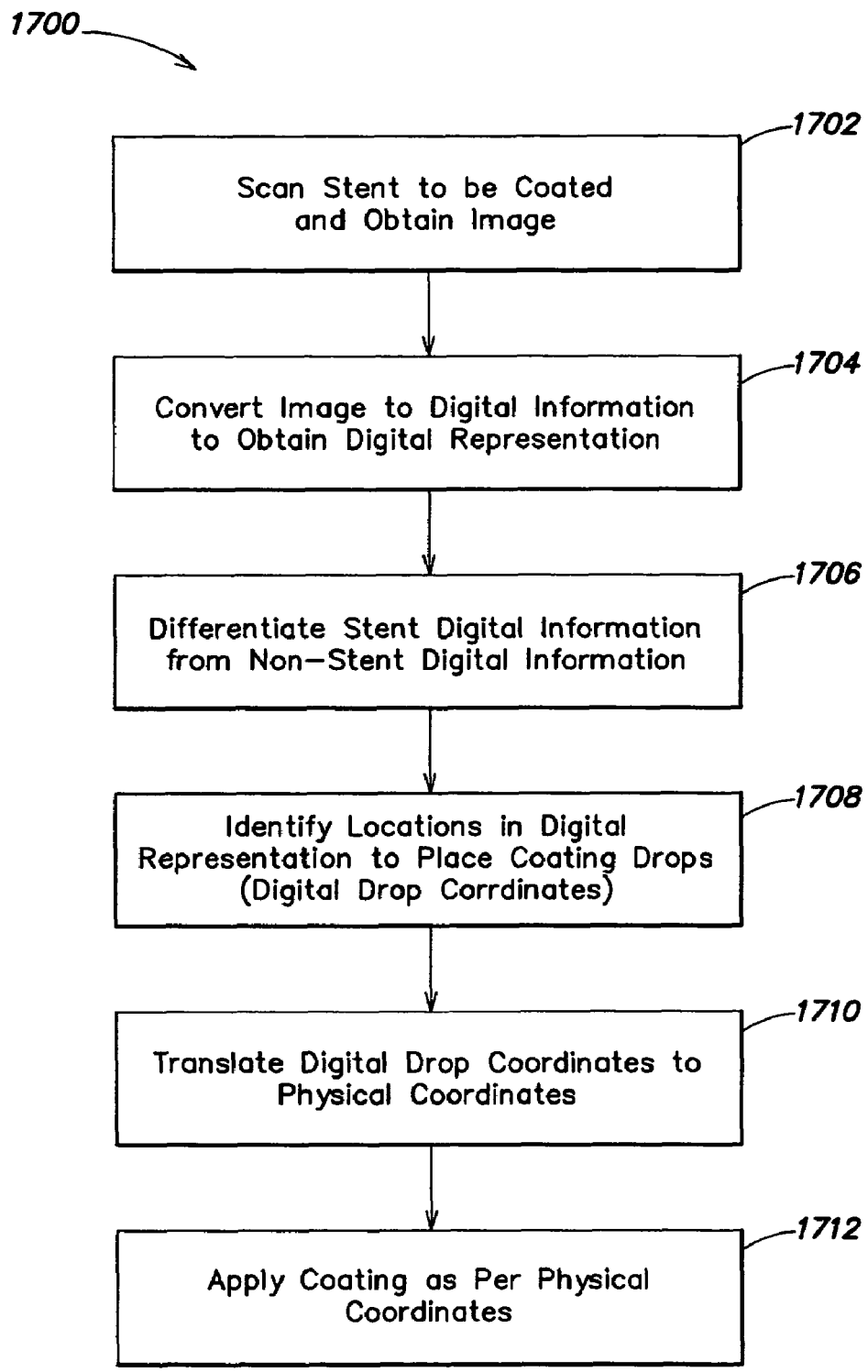
FIG. 17 is a flowchart of a coating method according to one embodiment of the present invention.

Another embodiment of the present invention includes a method 1700 for capturing and processing information regarding a device, for example, a stent, to be coated, as shown in FIG. 17.

In the description to follow, reference is made to a stent as being the medical device on which the coating is placed. It should be understood, however, that the present invention is equally applicable to any number of medical devices on which a medicinal coating is desired. While the description references a stent, merely for purposes of clarity, the present invention is not limited to just coating stents.

Figure 18:
FIG. 18 is a captured image of a stent.

The stent is placed within the field of view of the imaging system and scanned in order to obtain a number of images that cover the whole surface of the target, step 1702. The obtained image is stored as digital information either in memory or on appropriate storage media. As part of the process, the image is converted to digital information to obtain a digital representation, step 1704. This digital representation may include, but is not limited to: generating an image for viewing of the stent and the structure it is mounted upon as shown, for example, in FIG. 18. It is not necessary, however, that an image be displayed for viewing by an operator. It should be noted that the image as shown in FIG. 18 is one of many that would be generated. The digital information is then processed in order to differentiate the digital information representing the stent from the digital information that represents the portion of the scan that is not a part of the stent, step 1706.

Once the stent information or data has been differentiated from non-stent data, the locations or coordinates at which coating material will be placed is determined, step 1708. Up to this point in the process, the representation of the stent has been maintained in the virtual or digital domain. That is to say, the representation of the stent and, therefore, the coating coordinates are represented as locations in the digital representation. Thus, at step 1710, these digital coordinates representing where the coating material is to be placed are translated to physical coordinates representing physical locations on the stent for depositing of the coating material. These physical, or actual, coordinates representing locations on the stent are used by the control system 1402 to actuate the coating application module 36 to apply drops of coating material at only the desired locations, step 1712.

Figure 19:
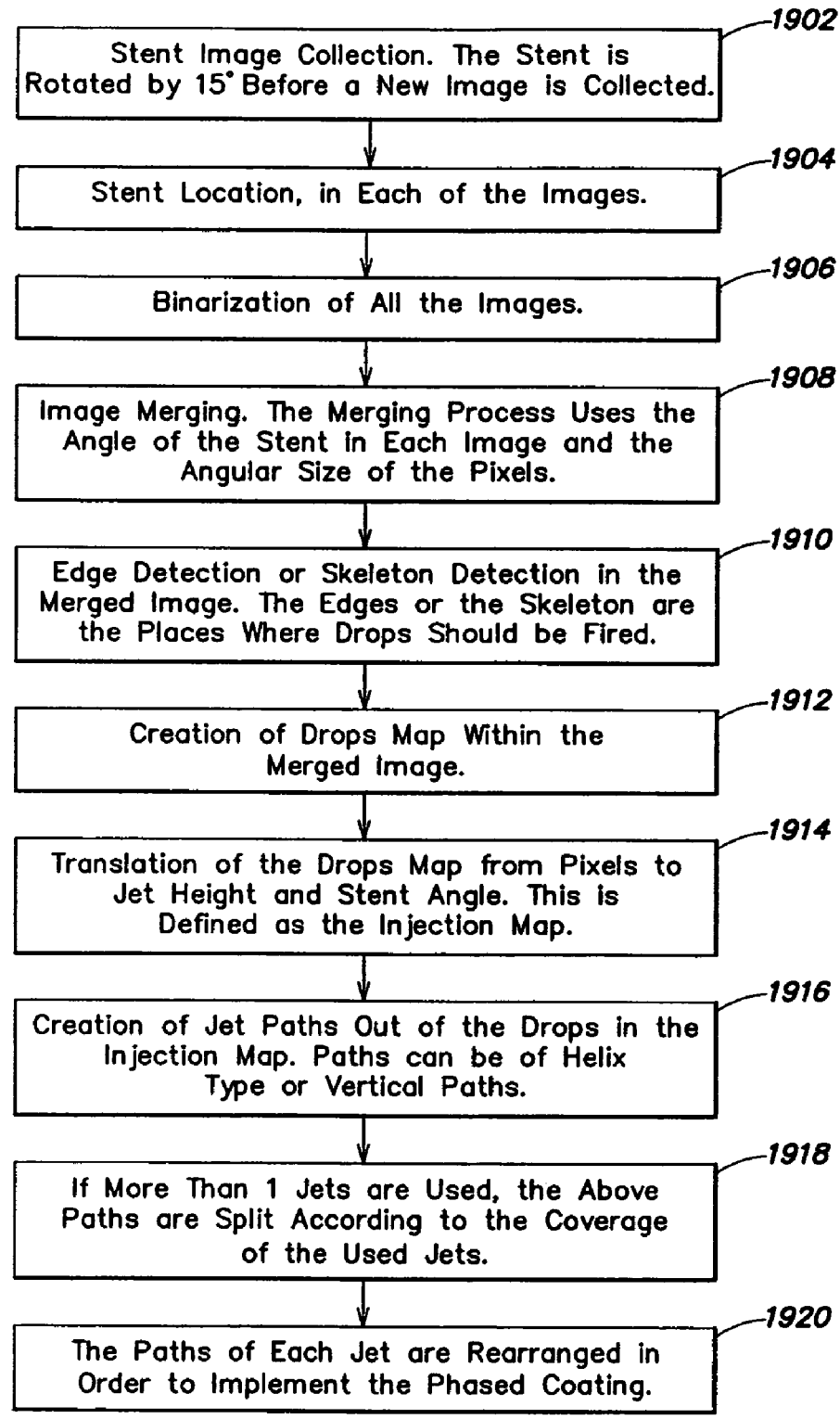
FIG. 19 is a flowchart of a coating method according to one embodiment of the present invention.

Details of the process generally described above with respect to FIG. 17 will now be described in more detail with respect to the flow chart and FIG. 19.

Figure 19A:
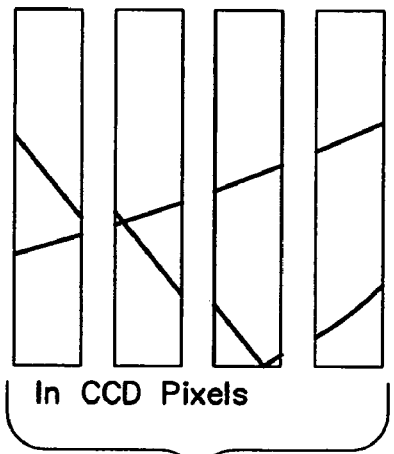

Multiple images of the stent are collected by rotating the stent around its axis, stopping the stent, capturing the image and then rotating in increments until a complete rotation has been obtained, step 1902. In one example, the stent is rotated by 15° for each image that is captured. The choice of the increment is not meant to be a limitation of the present invention and any increment suitable for obtaining multiple images around the circumference of the device is envisioned. As shown in FIG. 19A, multiple stent images, represented in CCD pixels, are obtained for each rotated section. In step 1904, the stent is located in each of the images. This involves processing the image data to distinguish the stent from any background. In addition, the stent axis is calculated in each image in order to measure rotational eccentricity, to be discussed further below.

Figure 19B:
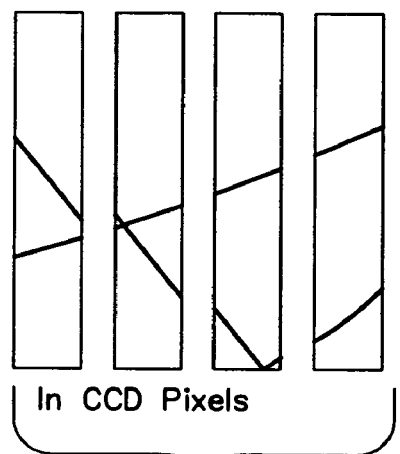
Figure 19C:
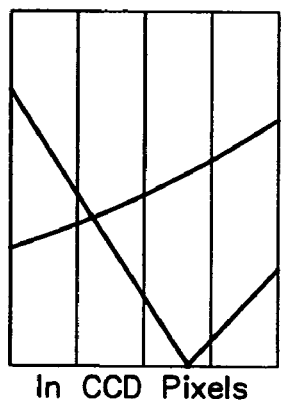
Figure 19D:
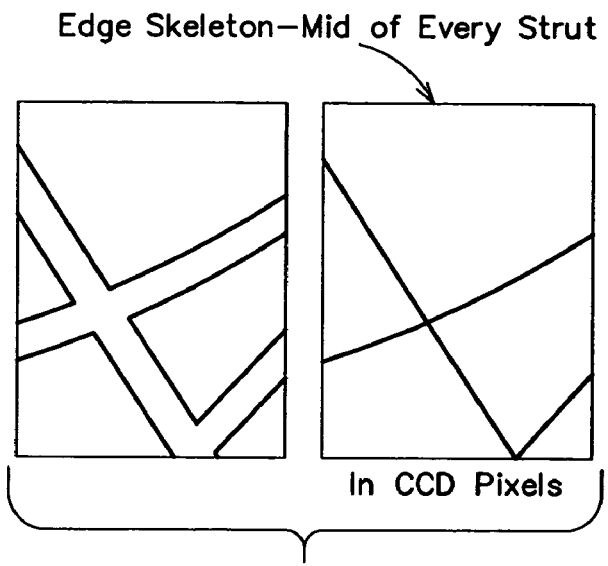

The central segment of the stent around the axis in each image is extracted. In one embodiment, the background may be a balloon catheter on which the stent is mounted or a mandrel configured to removably receive the stent. In this case, where a CCD imaging device has been used, the CCD pixels that represent the stent are located. Subsequently, all the images are binarized in that the CCD pixels that represent the stent are given a value different from the CCD pixels that do not represent the stent, step 1906 and FIG. 19B. The multiple images of the stent that have been captured and binarized are then merged in order to obtain an image of the stent, step 1908, FIG. 19C. The merging is accomplished, in one embodiment, according to the locations of the stent boundary in the different images. Although the boundaries do not appear in the merged image, they serve as indicators for relative position as an expected diameter of the stent is already known. In addition, any pixel that is identified as being part of the stent will be so identified in the merged image.

Once the images are merged to obtain a complete stent image, either edge detection or skeleton detection of the merged image is performed, step 1910. In skeleton detection, a mid-line of a stent strut is identified by processing of the merged stent image. There are any number of algorithms known to those of ordinary skill in the art for identifying midpoints of structures represented by digitized information.

Alternately, the edges of a stent strut can be detected. As is known, a stent strut includes an outer surface and an inner surface where the outer surface would be in contact with the vessel wall in which the stent is to be placed. Conversely, an inner surface of the stent would be in contact with the luminal flow, for example, blood, in a blood vessel. Each stent strut then includes side surfaces connecting the inner and outer surfaces. It is the edge points at the transition from the outer surface to an edge which are detected.

Figure 22A:
FIGS. 22A-22C are representations of a scanned stent according to an embodiment of the present invention.
Figure 22B:
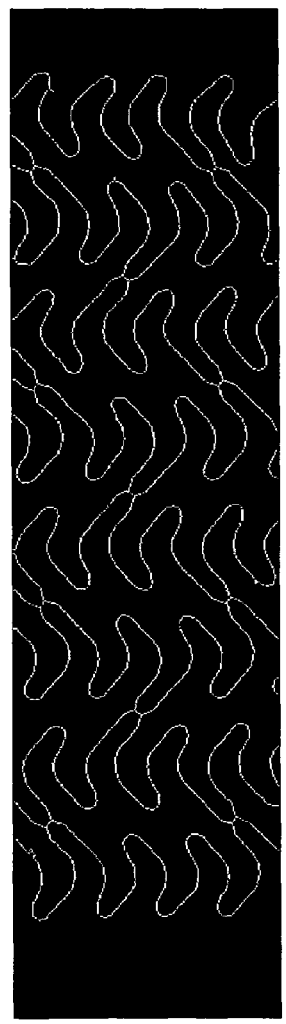
Figure 22C:
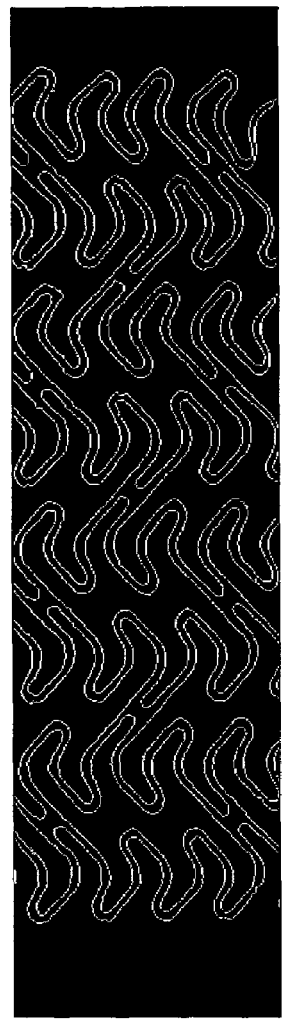

The images shown in FIGS. 22A-22C represent scanned stent data that has been binarized such that the portion of the image in white represents the stent and the black represents areas that are not stent (FIG. 22A); the results after a determination of the midline (FIG. 22B) has been performed where the white portion represents the midline, and a representation of the edges that have been detected where, as per before, white represents the location of the edge pixels in the image (FIG. 22C). As is known in the art, any one or more of Zhang and Suen's thinning algorithm, Stentiford's pre-processing algorithm or Holt's post-processing algorithm may be used.

Figure 19E:
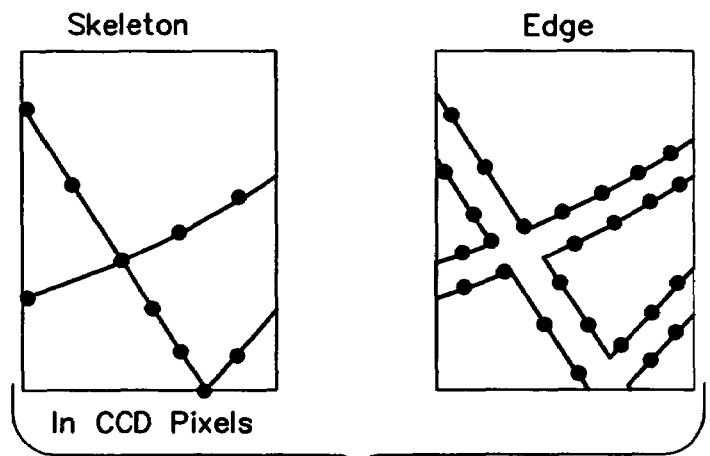

A drop map identifying where discrete drops of coating material are to be placed is then generated, step 1912. In one embodiment of the present invention, the drops are placed along the midline of the stent strut, as identified by the skeleton detection in step 1910. Alternatively, the coating material drops are placed along the identified edge locations of the stent strut. A general representation of skeleton placement and edge placement is shown in FIG. 19E. Of course, one of ordinary skill in the art would understand that the present inventors envision that the coating coordinates could include portions of the stent where the coating is placed along the edge only, or on the midline only, or a combination of edge and midline or have portions of the stent where no coating is to be placed.

Appropriate placement of the coating material at the edge of the stent strut facilitates the placement of coating on the side surfaces of the stent strut. Selection of the coating material characteristics including, but not limited to, viscosity, density, temperature, velocity, etc., allows for coating of the stent on the outer surface and the side surface without placing coating on the inner surface. Placing coating on the sides of the struts makes it possible to deliver more medicine to the patient. In some instances, however, it has been known that the depositing of coating material on an inner surface, especially where a stent is mounted on a balloon catheter, may interfere with the release of the stent from the balloon surface due to coating adhesion. Further, in some applications, the interior surfaces of the stent are coated. In accordance with one embodiment of the present invention, coating with specific characteristics such as viscosity and temperature positioned on the strut sides will spread and merge on to the interior surfaces.

The locations of the stent edges, from the image data, represent the optically or visually detected edge, i.e., that point or those points representing a boundary of the stent. These edge locations or coordinates, as above, can be used as the actual drop positions. In an alternate embodiment, these edge locations or coordinates are used as reference locations from which the drops can be either shifted toward the inside, here defined as toward the medial axis or shifted outside, i.e., away from the medial axis, according to the desired characteristics of the coating. The magnitude and direction of any shift can be changed as a function of the local geometry of the stent where, for example, curvature or shape may dictate direction or magnitude of shift.

Figure 19F:
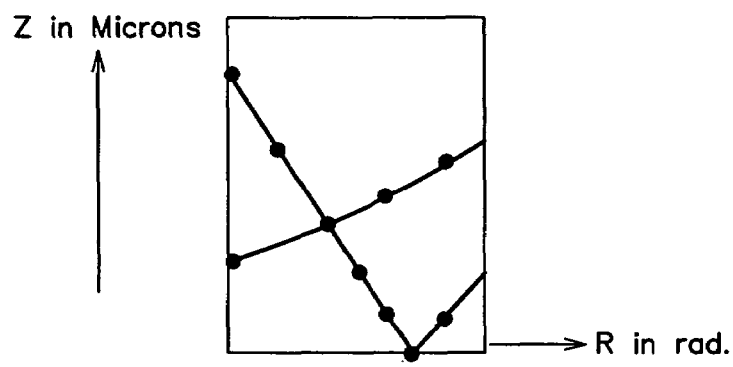
Figure 19G:
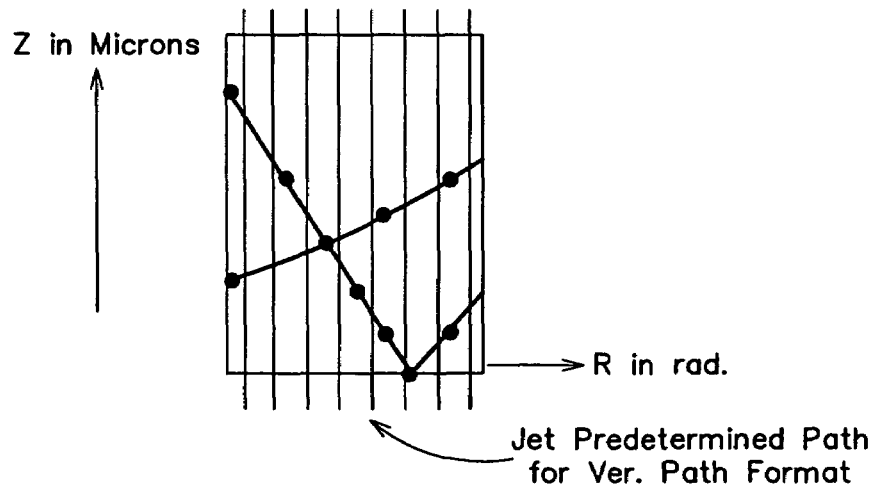

As discussed above, in step 1914, the drop coordinates in the drop map generated in step 1912 are translated from pixels with, for example, X, Y coordinates, to jet height and stent angle Z, R, step 1914. In this embodiment, the physical coordinates for the locations at which drops of coating material are to be placed are expressed as a Z, R pair where the Z coordinate, which could be measured in microns, represents a point along a longitudinal length of the stent, where a known location has been chosen as an origin and the R coordinate represents, in radians or degrees, a particular angular location around the circumference of the stent, once again where an angular origin has been defined, FIG. 19F.

As per the present invention, there are two paradigms of coating paths: a linear path and a helical path. Each of these will be described in more detail below.

As described above, a path which the coating applicator traces over the stent surface is independent of the coating pattern and the topology of the stent. In one embodiment, the coating applicator follows a linear path, substantially parallel to the longitudinal axis of the stent, across the surface of the stent. When the coating applicator, while following this linear path, intersects a coordinate from the injection map or drop map, then a drop of coating material is placed on the stent. At step 1916, the coating coordinates generated in step 1914 are placed in a sequence to facilitate the placement of the coating material when the applicator moves in a raster-based or linear motion over the stent. In the linear or raster paradigm, the injection map is scanned vertically to create a raster of vertical coating routes. An angular difference between adjacent vertical routes defines the angular resolution of the coating. This angular difference has a limit due to the difference between the injection times of two drops at the same height Z, in adjacent routes. This time difference is chosen to be greater than a certain value to prevent running of the coating as it is drying.

An alternate embodiment of the present invention, with respect to the linear path coating paradigm, maintains the angular resolution in order to prevent the coating from running by introducing a phase difference, referred to as linear phasing.

In linear phasing, an angular difference, about the stent circumference, between adjacent vertical routes is set to a value that prevents running of the coating for adjacent drops of material. As a result, the coating resolution is improved by repeating the raster path coating several times over the surface of the stent, each time in a slightly different phase.

As a non-limiting example, if an angular difference between adjacent raster scans is 1°, that same scan can be repeated four times with a phase shift of ¼°, creating four different raster scans with an overall angular resolution of ¼°. As a non-limiting example, starting at an origin angular location, 0°, the applicator moves along the length of the stent from one end to the other depositing material at locations as defined by the injection map, the stent is then rotated to the 1° location, then a return scan for depositing and this is repeated around the stent back to 0°. The stent is then rotated to place the applicator over the ¼° location, a linear scan is performed, the stent is rotated to 1¼°, scan, etc. around the circumference in 1° 1 steps and back to where it started, i.e., ¼°. This is repeated starting at ½°, around in 1° increments and then at ¾°, and around. Thus, while the angular resolution is increased, because of the phasing, there is no degradation of drops at the same Z in adjacent scans because of the time between deposition.

If more than one application jet is used in step 1918, the paths are divided so that the coordinates that fall within each application jet are assigned correspondingly.

Figure 20:
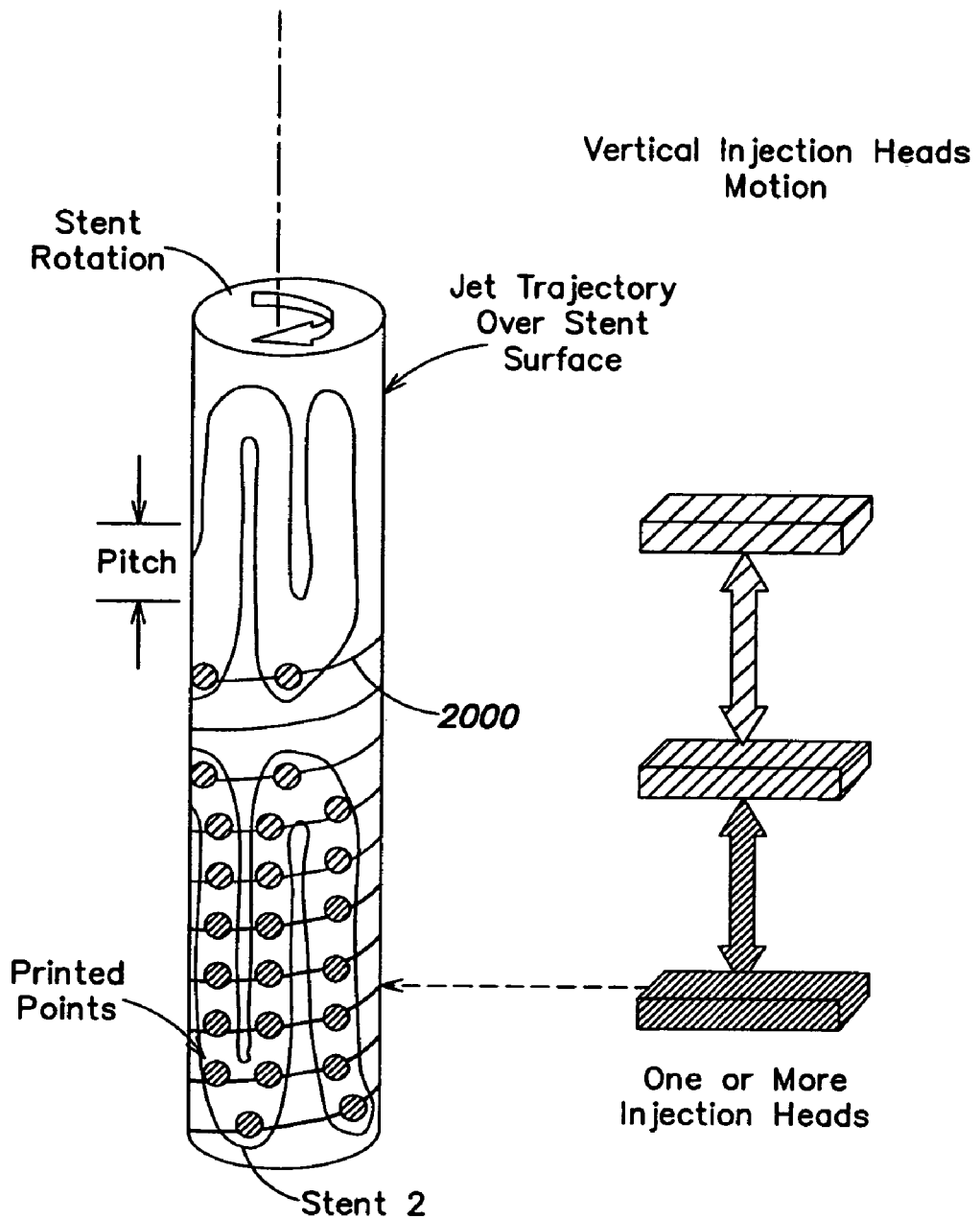
FIG. 20 is a schematic block diagram of the coating mechanism according to one embodiment of the present invention.

In another embodiment, with reference to FIG. 20, one or more injection heads of the coating applicator trace a helical path 2000. The helical path 2000 may result from a linear motion of the coating applicator substantially parallel to the longitudinal axis of the stent in combination with the rotation of the stent about its axis. The jet path generated in step 1916 for a helical relative motion of the coating applicator over the stent would be configured to allow for firing of the coating applicator when the coating applicator is located over a coordinate at which a drop of coating material is to be deposited.

Figure 21:
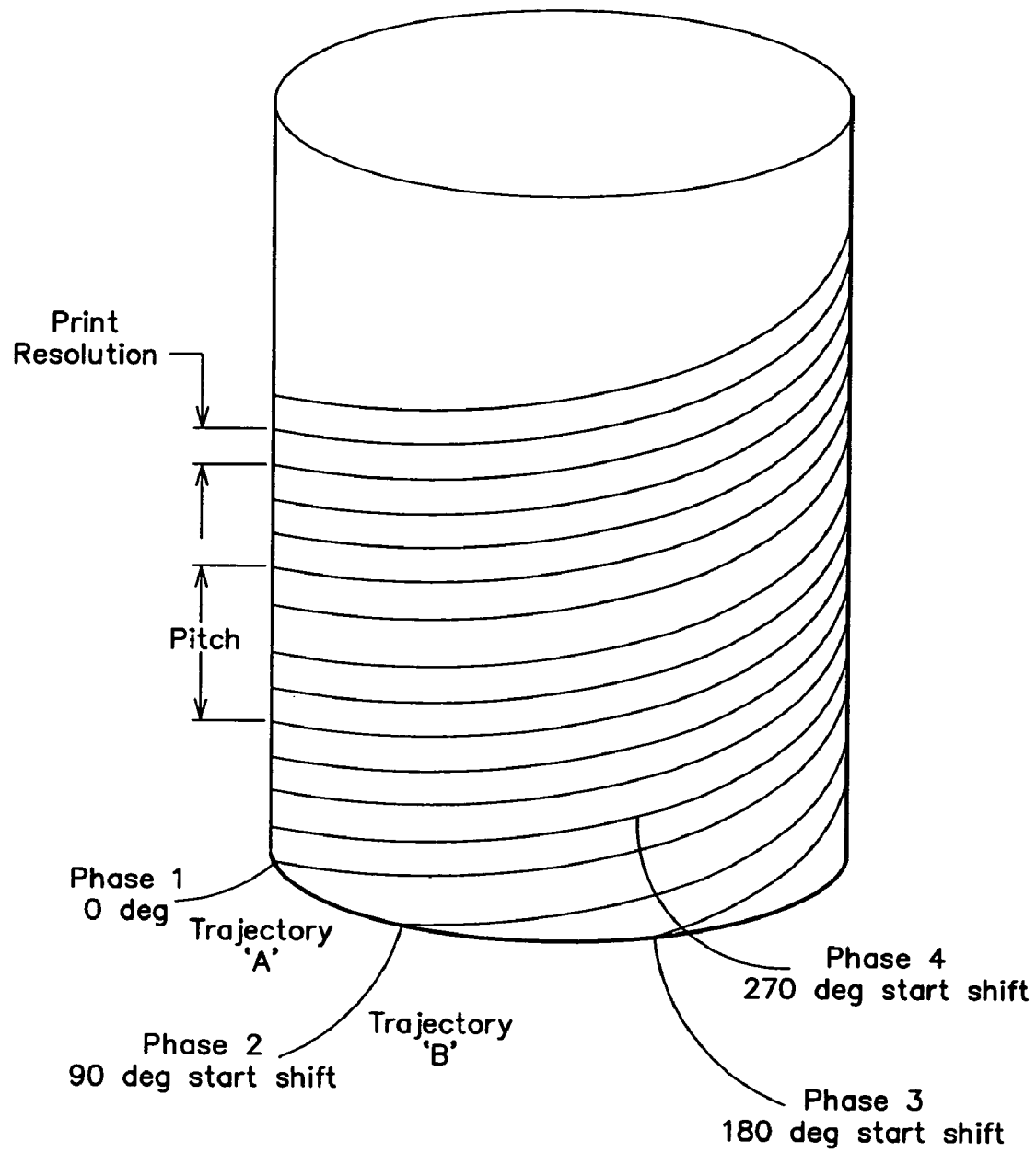
FIG. 21 is a representation of helical phased coating according to one embodiment of the present invention.

In one embodiment of the present invention, relative to the helical deposition of coating material, multiple helical paths, offset by a known phase from one another, may be defined for placing the discrete drops of coating material as schematically shown in FIG. 21. Using phased helical paths to deposit drops of coating material on the stent surface, the drops may be positioned closer to one another and more accurately by multiple helical passes. With this method, similar to the phased linear approach above, drops of material that have already been deposited are sufficiently dried so that subsequent drops may be placed much closer or even overlap without dislodging the already placed material. The number of helical passes and, therefore, the phase difference therebetween may be chosen by the user to define the coating passes. The coating coordinates are then ordered in a sequence that will accommodate the helical deposition.

In the helical paradigm, the injection map is diagonally scanned to create a helical coating route. As above, the helical route can be the result of rotation of the stent concurrent with linear movement of the coating applicator. A vertical step per one turn of the helix path defines a vertical resolution of the coating. This vertical step has a lower limit due to the difference between the injection times of two drops at the same angle, in successive turns of the helix. Once again, this time difference should be greater than a certain value to prevent running. In order to keep vertical resolution high enough, and keep the helix vertical step above the limit, one embodiment of the present invention is directed to helical phasing.

In helical phasing, the helix vertical step is kept high enough to prevent running. The coating resolution is optimized by repeating the helix several times, each time starting at a different angle phase. As a non-limiting example, if the helix vertical step is 40 microns, it can be repeated four times with a phase shift of 90° in the helix starting point, creating four different helical routes with overall vertical resolution of ten microns.

To facilitate multiple layers of coating material, a number of complete passes over the device can be programmed and the coating applicator will complete that number of multiple passes. Alternately, where the coating layers are of different materials, a first injection map for one material may be generated and a second injection map generated for the next layer. It is not necessary that the same points are chosen in each layer. According to an aspect of the present invention, inkjet applicators may be dedicated to specific materials and switched in and out according to the coating requirements.

In another embodiment of the present invention, geometric characteristics of a stent topology are detected and identified. Once detected and identified, the locations of these geometric attributes, i.e., the CCD pixel locations and the corresponding physical locations are obtained. The characteristics of the coating material to be placed at these identified geometric locations are adjusted accordingly.

In one non-limiting example, where it is known that a large amount of stress may be incurred on the stent, upon, for example, expansion, then either more or less of the coating material may be deposited at that location. In one embodiment, a filtering operation is performed to remove or add coating points at a specific area of the stent. Further, for example, at the distal and proximal ends of the stent where it is more likely that irritation of the vessel in which the stent is placed can occur, a different formula of the coating material may be placed. In accordance with the present invention, any number of different characteristics of the coating material may be adjusted depending upon the detected geometric characteristic of the stent including, but not limited to, changing the drop size, changing the material composition, depositing more than one drop of one material at each location in the area, adjusting the temperature of the material to be placed, adjusting the areal density of the drops at that area, placing multiple layers of material, etc.

Upon the detection and identification of a local geometric characteristic of the stent, in accordance with one embodiment of the present invention, any one or more of: a thickness of a coating, a number of layers of a coating, and coating material choice may be adjusted. Further, areas to be masked, i.e., an area in which no coating material will be deposited can also be determined. In the event of masking, no coating points will be defined for one or more portions of the stent or medical device.

Figure 23:
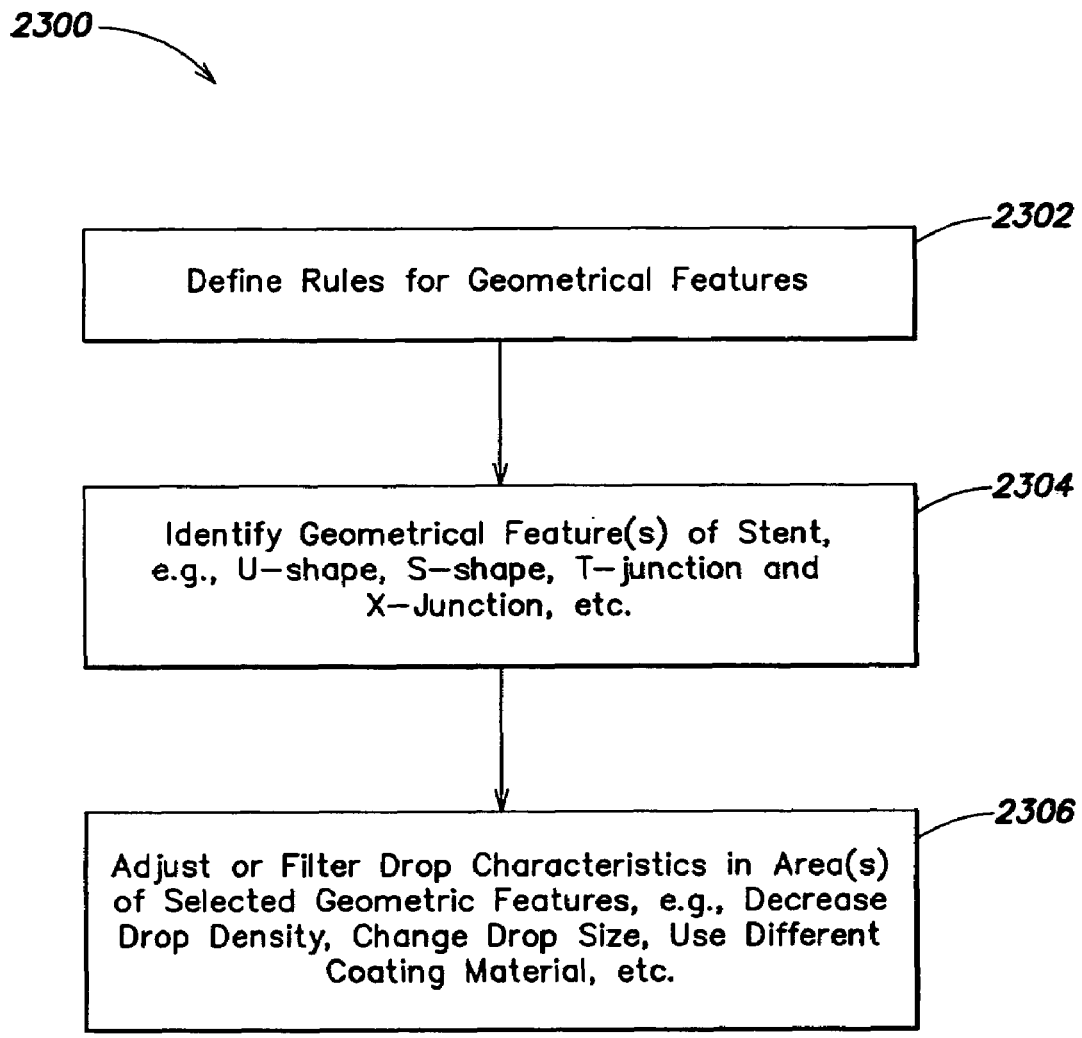
FIG. 23 is a flowchart for coating according to geometric features according to one embodiment of the present invention.
Figure 24B:
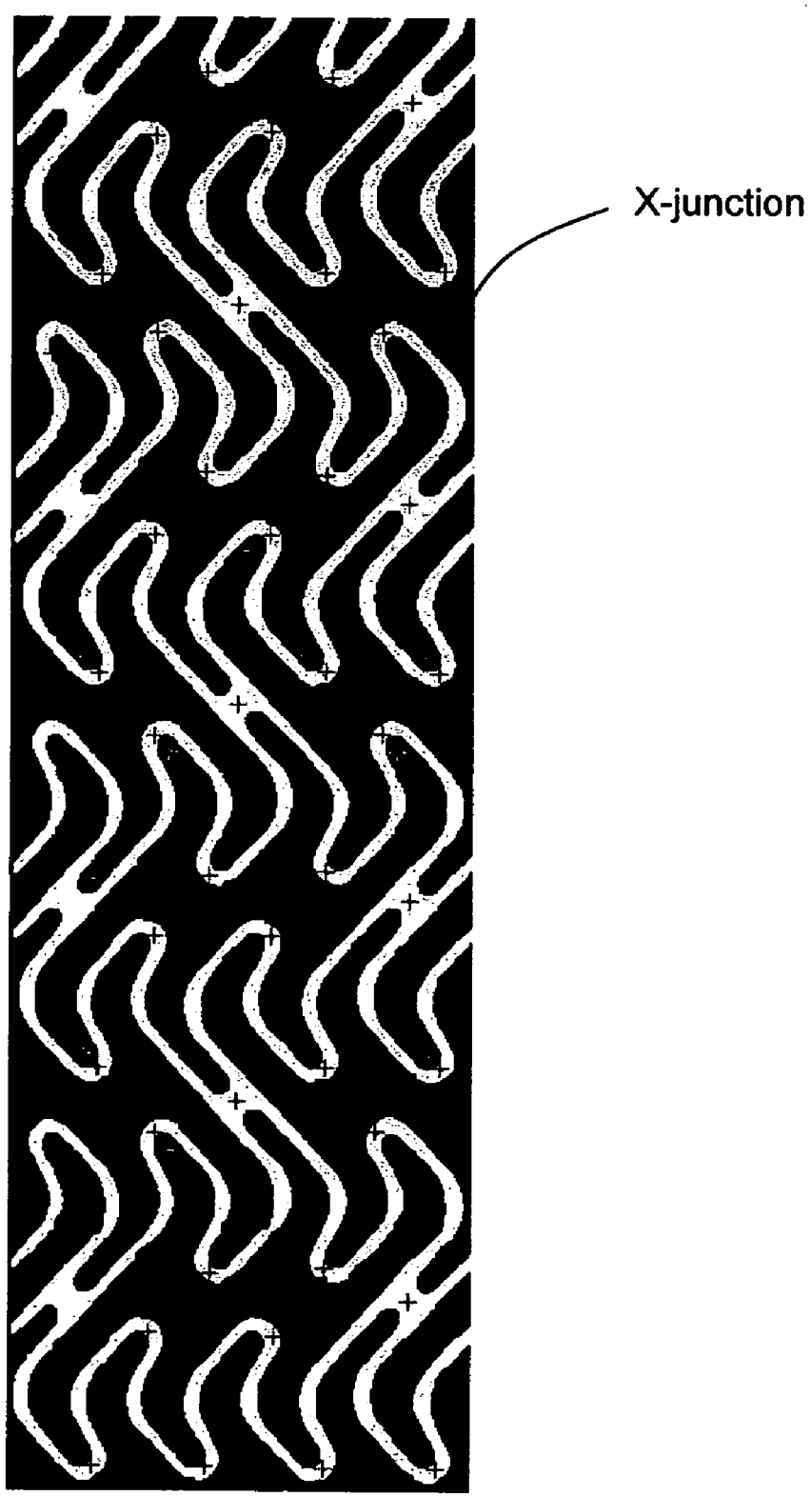

In accordance with a method 2300 of this aspect of the present invention, at step 2302, as shown in FIG. 23, rules for specific geometric features are established. These rules may be obtained by empiric observation or from actual measurement. At step 2304 the geometrical features are identified, for example, a U-shape, S-shape, T-junction or an X-junction as shown in FIGS. 24A and 24B. In step 2306, as above, the drop characteristics can be adjusted for the areas of the selected geometric features.

As one non-limiting example, it has been determined that a decrease in density of coating material in a vicinity of U-shaped struts is beneficial. A parameter can be selected by the user to adjust for a curvature factor of the U-shape and the extent of its influence, i.e., how far away from the U-shape the coating density should be adjusted. In addition, a decrease in density of the coating material in the vicinity of an X-junction or a T-junction provides better coating performance on the stent.

While representative examples of geometric configurations have been identified, the present invention is not limited to only these shapes or junctions. Any geometry that can be identified as warranting an adjustment to coating parameters is encompassed by the present invention.

In an alternate embodiment, a user, e.g., a physician, prior to a procedure, may identify portions of the stent at which coating material parameters are adjusted. As an exemplary embodiment of the present invention, a representation of the scanned stent may be presented on a display screen. Through a user interface, perhaps a touch screen or light pen or similar pointing device, the physician identifies areas of the stent and characteristics thereof. In one example, the physician may choose a medicinal coating of a certain type for placement in an intermediate portion of the stent and a different material at the proximal and distal portions. Any one or more of a number of parameters could be adjusted or chosen by the physician including, but not limited to, medicine, areal density, number of layers of coating material and a temperature at which the coating is ejected. In addition, global parameters could be selected, for example: sections of the stent could be selected where the coating is placed on the medial line of the stent but in other sections the coating is placed at the edges. The magnitude and direction for edge coating offset can also be selected on a global basis, i.e., either for the entire stent or portions thereof.

Once the parameters have been chosen and set by the physician, the present invention will convert the information into the injection map for controlling the ink jet applicator. In an alternate embodiment, the physician may be able to select either helical or raster application or, depending upon the parameters that were set, the system might allow some parameters to be user-selectable but not others.

Further, pre-defined coating schemes may be created to use as a template for the coating of a stent. Where, for example, a physician has obtained repeated success with a particular coating scheme, it could be repeated on subsequent stents. The system, as it scans each stent individually, would then apply the parameters of the coating and generate the injection map, i.e., the coordinates where coating material is deposited accordingly. Still further, a stent may be coated per a prescription issued by the physician to a pharmacy with a stent coating system.

As a relatively straight-forward example, a physician may determine that stents having a density A of material B in the central third of the device and a density C at the proximal and distal remaining portions provides beneficial results. She could then enter these general requirements and the system of the present invention would identify the coordinates of the stent that falls within the portions, define the injection map and then coat the stent accordingly.

A calibration procedure is performed on the system to ensure accurate conversion of the CCD pixels to the physical coordinates of the stent or device to be coated. In accordance with a calibration procedure 2500 represented in FIG. 25, a predefined pattern of points is injected on a calibration target, step 2502, using an injection material visible to the camera. These points are injected at known locations per Z,R coordinates, i.e., angular position—around the target and linear position along its length, as described above. Images of these points are collected, step 2504, from several different angles around the device. The choice of the number of different angles is not limiting as long as a sufficient number are chosen to obtain the necessary calibration points. The positions of the drops on the calibration target are determined, step 2506, and the positions in the images are detected, step 2508. A transformation from the image pixels to the known physical locations is then calculated, step 2510. As it is known where the drops were intended to be positioned and where the drops' positions were detected, a minimum square-error fitting process is performed and the parameters or calibration data of the transformation are calculated and saved, step 2512.

Figure 25:
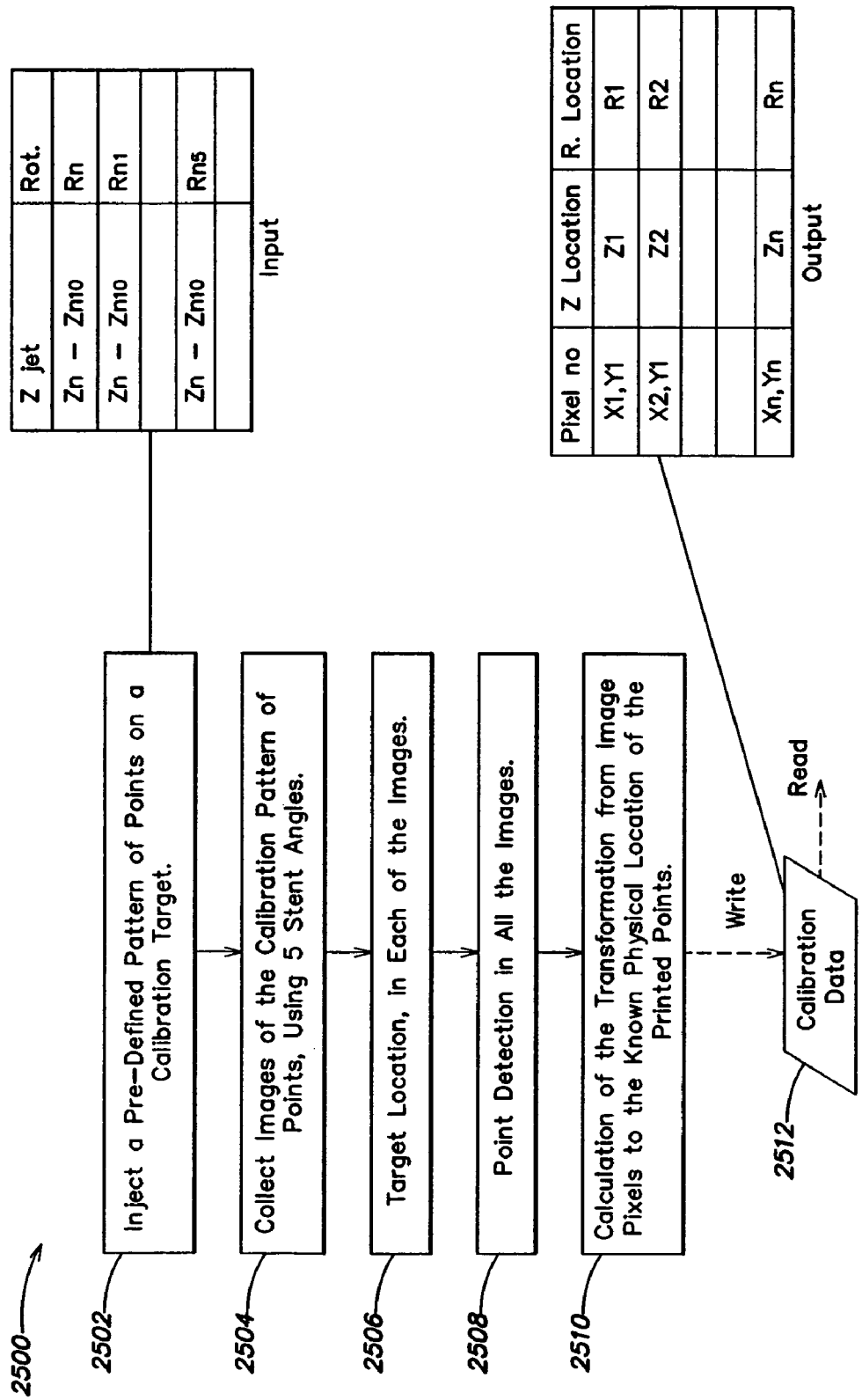
FIG. 25 is a flowchart of a calibration procedure in accordance with one embodiment of the present invention.

As shown in FIG. 25, in one embodiment of the present invention, a mapping table that maps one or more pixels with respective X,Y coordinates to a location on the stent with Z,R coordinates is maintained for the system. Alternatively, if the fitting or calibration determines that the behavior of the system can be expressed as a function or formula, then the formula would be stored and a mapping table would not be used. As is understood by one of ordinary skill in the art, the calibration process can be performed on a regular schedule to account for any system drift that might occur.

In embodiments of the present invention, either a "bare" stent or one that is mounted on a balloon catheter may be coated. In the case of the bare stent, it is mounted directly on a mandrel for positioning within the system. In a system operating with the mandrel-mounted stent, all components are rotating concentrically about the same axis, that is, the stent rotates about the axis of the system.

The same concentric rotation may not be present with a stent mounted on a balloon catheter. As has been described above, a stent mounted on a balloon catheter may be "off-center" relative to a longitudinal axis of the balloon catheter due to the crimping process. The crimping process is not so exact that the stent is mounted on the balloon such that the stent and the balloon catheter's guide wire lumen are concentric. Often, there is an eccentricity that is introduced by the crimping process.

In one embodiment of the present invention, the balloon catheter would be mounted on a relatively stiff wire threaded through the guidewire lumen of the balloon catheter, i.e., a mandrel. While this mandrel is configured to rotate on the center axis of the system, compensation for the rotational eccentricity of the stent relative to the mandrel and, therefore, the system, has to be calculated.

Figure 26:
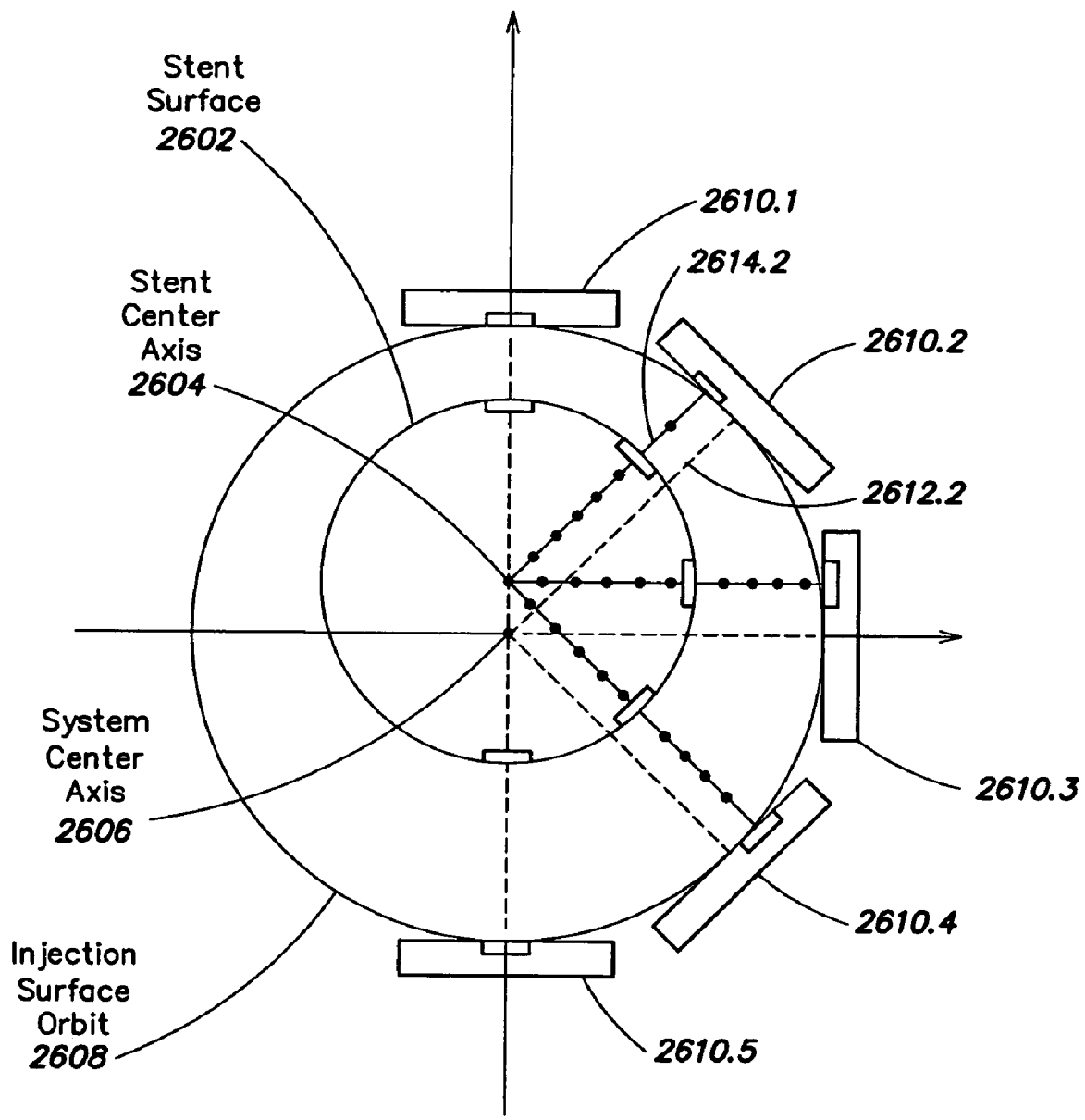
FIG. 26 is a schematic representation of a scanning procedure in accordance with one embodiment of the present invention.

The compensation for the rotational eccentricity will be described with respect to FIG. 26 which is a cross-section of the stent, at one Z location along its length, mounted on a balloon catheter that is mounted on a mandrel. A stent surface 2602 rotates about a stent center axis 2604. A system center axis 2606 is defined by the mandrel of the system and an injection surface orbit 2608 represents the orbit around the stent in which the applicator can move. As above, the applicator rotates around the system center axis 2606 in the injection surface orbit 2608. It should be noted that the representation of the applicator rotating can be accomplished by either rotating the stent with the applicator remaining stationary or moving the applicator around the stent or a combination of these movements. The description here is meant to describe the compensation process and not limit any embodiments of the present invention.

The stent surface 2602 is the actual surface of the stent and, as above, is not necessarily centered at the system center 2606. The stent center axis 2604 may also be at a different point at different Z locations along the length of the stent. The location of the stent axis is located in each of the images 2610.1-2610.5. As a representative example, referring to the image 2610.2, the system center axis 2606 is located in the center of the image 2610.2, as would be expected because the imaging system is concentric with the system center axis 2606 and represented by a dashed line 2612.2. The location of the stent center axis in the image 2610.2 is determined by detected the boundary of the stent in the image and finding the center of that detected boundary. As shown in FIG. 26, the center axis of image 2610.2 is located along dotted line 2614.2. By operation of this method, the location of the stent axis is calculated as a function of Z.

The central stent section (dotted lines) are detected in each image 2610. As has already been described above, the central segments are merged to create the stent surface image. The merged stent surface image is processed in order to extract the injection points and converted from the CCD coordinate system to the stent coordinate system.

The present invention teaches a method for coating a prosthesis as well as an apparatus for coating a prosthesis, a system for coating a prosthesis, and an application control module for coating a prosthesis.

Embodiments of the above-described invention may be implemented in either all software, all hardware, or a combination of hardware and software, including program code stored in a firmware format to support dedicated hardware. A software implementation of the above described embodiment(s) may comprise a series of computer instructions either fixed on a tangible medium, such as a computer readable media, e.g. diskette, CD-ROM, ROM, or fixed disk or transmittable to a computer system in a carrier wave, via a modem or other interface device. The medium can be either a tangible medium, including but not limited to optical or analog communications lines, or may be implemented with wireless techniques, including but not limited to microwave, infrared or other transmission techniques. The series of computer instructions whether contained in a tangible medium or a carrier wave embodies all or part of the functionality previously described herein with respect to the invention. Those skilled in the art will appreciate that such computer instructions can be written in a number of programming languages for use with many computer architectures or operating systems and may exist in machine executable format. Further, such instructions may be stored using any memory technology, present or future, including, but not limited to, semiconductor, magnetic, optical or other memory devices, or transmitted using any communications technology, present or future, including but not limited to optical, infrared, microwave, or other transmission technologies. It is contemplated that such a computer program product may be distributed as a removable media with accompanying printed or electronic documentation, e.g., shrink wrapped software, preloaded with a computer system, e.g., on system ROM or fixed disk, or distributed from a server or electronic bulletin board over a network, e.g., the Internet or World Wide Web.

Further, with respect to the control system 1402, it is envisioned that the control system 1402 could be implemented as a computer connected via a network to the applicator device 1. While the user may access the functions via a local terminal, the processing may be occurring remotely. Of course, one of ordinary skill in the art would understand the technical requirements for such a network to operate properly.

Still further, the applicator device 1 may be located remotely from the user and the parameters for coating are relayed to a central facility at which the device 1 is located. As an example, a hospital may have a centrally located stent coating facility within a same building as where the procedure is being performed on the patient or nearby on its campus. The physician/user may be able to enter the required parameters via a terminal or interface and the coating is then applied, the stent is delivered to the physician for insertion and the stent is inserted into a patient. This is similar to a just-in-time manufacturing process where components are ordered/created shortly before they are needed.

Although various exemplary embodiments of the present invention have been disclosed, it will be apparent to those skilled in the art that various changes and modifications can be made which will achieve some of the advantages of the invention without departing from the spirit and scope of the invention. It will be apparent to those reasonably skilled in the art that other components performing the same functions may be suitably substituted.

What is claimed is:

1. A method of coating a medical device, the method comprising:
    optically scanning the medical device and obtaining a plurality of views of the medical device;
    merging the plurality of views to generate a digital representation of the medical device;
    processing the generated representation to generate a topology of the medical device;
    determining a first plurality of reference locations on the generated topology wherein each location of the first plurality of locations corresponds to a location on the medical device at which at least one drop of coating material is to be placed;
    generating a second plurality of locations as a function of the first plurality of reference locations, wherein each location of the second plurality of locations defines a physical point on the medical device; and
    depositing at least one drop of coating material on at least one location in the second plurality of locations with an applicator, wherein the movement of the applicator relative to the medical device does not substantially follow the topology of the medical device.

2. The method as recited in claim 1, further comprising:
    rotating the medical device on its longitudinal axis such that each view of the plurality of views is of a different angular portion of the medical device.

3. The method as recited in claim 1, wherein the medical device is a stent comprising a plurality of struts and processing the generated representation to generate the topology comprises:
    detecting at least one of:
        an edge of a strut; and
        a mid-line of a strut,
    wherein the first plurality of locations are determined to lie along at least one of:
    the edge of a strut and the mid-line of a strut.

4. The method as recited in claim 1, further comprising:
    representing each location of the first plurality of locations as a function of pixels in a device used to scan the medical device; and
    converting each location of the first plurality of locations to a corresponding second plurality of physical locations on the medical device,
    wherein each location in the second plurality of locations comprises a linear component and an angular component.

5. The method as recited in claim 4, further comprising:
    ordering the second plurality of locations in a sequence to place the coating material drops on the medical device in a helical pattern when a coating applicator is moved in a helical path over the medical device.

6. The method as recited in claim 1, further comprising:
    merging the plurality of views to obtain a three-dimensional representation of the medical device.

7. The method as recited in claim 1, wherein each view of the plurality of views is from a different angular position about the circumference of the medical device.

8. The method as recited in claim 1, wherein the medical device is a stent comprising a plurality of struts, each strut having an exterior surface, interior surface and side surfaces therebetween, and wherein:
    generating the topology comprises detecting at least one edge of a strut,
    determining the first plurality of locations as being along the detected at least one edge of the strut; and selecting coating material characteristics such that coating material placed along the at least one edge of the strut flows to coat the side surfaces.

9. A method of loading a stent with a medicinal compound, the stent comprising a plurality of struts, the struts being in a geometric pattern, the method comprising:
scanning the stent to identify one or more edges of the struts;
determining a first set of coordinates for the indentified one or more edges of the struts;
generating a second set of coordinates as a function of the first set of coordinates; and
ejecting the medicinal compound at each coordinate in the second set of coordinates with an applicator, wherein the movement of the applicator relative to the stent does not substantially follow the geometric pattern of the struts.

10. The method of claim 9, wherein scanning the stent comprises:
optically scanning the stent; and
detecting an optical difference between a strut and anything not a strut.

11. The method of claim 10, wherein scanning further comprises:
capturing an image of the stent struts.

12. The method of claim 10, wherein generating the second set of coordinates comprises:
identifying coordinates for a surface of a strut form the first set of coordinates; and
generating the second set of coordinates as coordinates shifted from the first set of coordinates and away from the identified strut surface coordinates.

13. The method of claim 12, wherein ejecting the medicinal compound comprises:
ejecting the medicinal compound from an ink jet applicator.

14. The method of claim 10, wherein the optical difference is determined as a function of light reflecting off of the stent.

15. A method of loading a medicinal compound on a stent comprising a plurality of struts, the struts being in a geometric pattern, the method comprising:
illuminating the stent with light from a light source;
capturing an image of the illuminated stent;
processing the captured image and generating a first set of coordinates corresponding to edges of the stent struts;
processing the first set of coordinates to generate at least one bounded area coordinate in an area bounded by edges of the stent struts; and
directing at least one drop of the medicinal compound toward the at least one bounded area coordinate;
applying the drop with an applicator, wherein the movement of the applicator relative to the stent does not substantially follow the geometric pattern of the struts.

16. The method of claim 15, wherein capturing an image comprises:
storing the captured image as digital information; and
processing the captured image comprises differentiating the stored digital information representing the stent struts from the stored digital information that represents a part of the captured image that is not a stent strut.

17. The method of claim 16, wherein capturing an image of the illuminated stent comprises:
optically scanning the stent.

18. The method of claim 15, wherein directing at least one drop of the medicinal compound comprises:
ejecting the at least one drop from an ink jet device.

19. The method of claim 18, further comprising:
positioning the ink jet device substantially at the at least one bounded area coordinate prior to ejecting the at least one drop.

* * * * *